US007820684B2

(12) United States Patent
Bearss et al.

(10) Patent No.: US 7,820,684 B2
(45) Date of Patent: Oct. 26, 2010

(54) PHARMACEUTICAL FORMULATIONS COMPRISING SALTS OF A PROTEIN KINASE INHIBITOR AND METHODS OF USING SAME

(75) Inventors: David J. Bearss, Cedar Hills, UT (US); Rajashree Joshi-Hangal, Pleasanton, CA (US); Xiao-Hui Liu, Sandy, UT (US); Pasit Phiasivongsa, Brentwood, CA (US); Sanjeev G. Redkar, Hayward, CA (US); Hariprasad Vankayalapati, Draper, UT (US)

(73) Assignee: SuperGen, Inc., Dublin, CA (US)

( * ) Notice: Subject to any disclaimer, the term of this patent is extended or adjusted under 35 U.S.C. 154(b) by 0 days.

(21) Appl. No.: 12/041,565

(22) Filed: Mar. 3, 2008

(65) Prior Publication Data

US 2008/0226747 A1    Sep. 18, 2008

Related U.S. Application Data

(60) Provisional application No. 60/892,373, filed on Mar. 1, 2007, provisional application No. 60/911,789, filed on Apr. 13, 2007.

(51) Int. Cl.
*A01N 43/54* (2006.01)
*A61K 31/505* (2006.01)
(52) U.S. Cl. .................................... 514/267
(58) Field of Classification Search ............ 514/267
See application file for complete search history.

(56) References Cited

FOREIGN PATENT DOCUMENTS

WO    WO 2005/037825    *    4/2005
WO    WO 2005/037825 A2    4/2005

OTHER PUBLICATIONS

Berge, et al., Pharmaceutical Salts, J. of Pharm. Sciences (1977).*
Advani, "FLT3 and Acute Myelogenous Leukemia: Biology, Clinical Significance and Therapeutic Applications," Current Pharmaceutical Design 11(26): 3449-3457, 2005.
Alexis et al., "An immunohistochemical evaluation of c-kit (CD-117) expression in malignant melanoma, and results of imatinib mesylate (Gleevec) therapy in three patients," Melanoma Research 15(4): 283-285, 2005.
Alvarez et al., "Biology of Platelet-Derived Growth Factor and Its Involvement in Disease," Mayo Clinic Proc 81(9): 1241-1257, Sep. 2006.
Blume-Jensen et al., "Activation of the human c-kit product by ligand-induced dimerization mediates circular actin reorganization and chemotaxis," The EMBO Journal 10(13): 4121-4128, 1991.
Corbin et al., "In vitro and in vivo activity of ATP-based kinase inhibitors AP23464 and AP23848 against activation-loop mutants of Kit," Blood 106(1): 227-234, Jul. 1, 2005.
Corless et al., "PDGFRA Mutations in Gastrointestinal Stromal Tumors: Frequency, Spectrum and In Vitro Sensitivity to Imatinib," J Clin Oncol 23(23):5357-5364, Aug. 10, 2005.
Daboussi et al., "DNA double-strand break repair signalling: The case of RAD51 post-translational regulation," Cellular signalling 14: 969-975, 2002.
De Giorgi and Verweij, "Imatinib and gastrointestinal stromal tumors: Where do we go from here?", Mol Cancer Ther 4(3): 495-501, Mar. 2005.
Foster et al., "Molecular basis of the constitutive activity and STI571 resistance of Asp816Val mutant KIT receptor tyrosine kinase," Journal of Molecular Graphics and Modelling 23: 139-152, 2004.
Frost et al., "Juxtamembrane Mutant V560GKit Is More Sensitive to Imatinib (STI571) Compared with Wild-Type c-Kit Whereas the Kinase Domain Mutant D816VKit Is Resistant," Molecular Cancer Therapeutics 1: 1115-1124, Oct. 2002.
Gotlib et al., "Activity of the tyrosine kinase inhibitor PKC412 in a patient with mast cell leukemia with the D816V Kit mutation," Blood 106(8): 2865-2870, Oct. 15, 2005.
Growney et al., "Activation mutations of human c-KIT resistant to imatinib mesylate are sensitive to the tyrosine kinase inhibitor PKC412," Blood 106(2): 721-724, Jul. 15, 2005.
Hansen et al., "The Role of RAD51 in Etoposide (VP16) Resistance in Small Cell Lung Cancer," Int J Cancer 105: 472-479, 2003.
Heinrich et al., "Biology and Genetic Aspects of Gastrointestinal Stromal Tumors: KIT Activation and Cytogenetic Alterations," Human Pathology 33(5): 484-495, May 2002.
Heinrich et al., "Inhibition of KIT Tyrosine Kinase Activity: A Novel Molecular Approach to the Treatment of KIT-Positive Malignancies," J Clin Oncol 20(6): 1692-1703, Mar. 15, 2002.
Henning and Stürzbecher, "Homologous recombination and cell cycle checkpoints: Rad51 in tumour progression and therapy resistance," Toxicology 193: 91-109, 2003.

(Continued)

*Primary Examiner*—James O Wilson
*Assistant Examiner*—Erich A Leeser
(74) *Attorney, Agent, or Firm*—Seed IP Law Group PLLC

(57) ABSTRACT

The present invention relates to pharmaceutical formulations comprising the protein kinase inhibitor, MP470, and methods of using same in treating conditions involving undesirable cell proliferation, such as cancer.

13 Claims, 12 Drawing Sheets

OTHER PUBLICATIONS

Hirota et al., "Gain-of-Function Mutations of c-kit in Human Gastrointestinal Stromal Tumors," Science 279: 577-580, Jan. 23, 1998.

Juurikivi et al., "Inhibition of c-kit tyrosine kinase by imatinib mesylate induces apoptosis in mast cells in rheumatoid synovia: a potential approach to the treatment of arthritis," Ann Rheum Dis 64: 1126-1131, 2005.

Qiao et al., "High-level expression of Rad51 is an independent prosnostic marker of survival in non-small-cell lung cancer patients," British Journal of Cancer 93(1): 137-143, 2005.

Schmidt-Arras et al., "Flt3 Receptor Tyrosine Kinase as a Drug Target in Leukemia," Current Pharmaceutical Design 10(16): 1867-1883, 2004.

Tian et al., "Activating c-kit Gene Mutations in Human Germ Cell Tumors," Am J Pathol 154(6): 1643-1647, Jun. 1999.

Yarden et al., "Human proto-oncogene c-kit: a new cell surface receptor tyrosine kinase for an unidentified ligand," The EMBO Journal 6(11): 3341-3351, 1987.

* cited by examiner

PHARMACEUTICAL FORMULATIONS COMPRISING SALTS OF A PROTEIN KINASE INHIBITOR AND METHODS OF USING SAME

CROSS-REFERENCE TO RELATED APPLICATION

This application claims the benefit under 35 U.S.C. §119 (e) of U.S. Provisional Patent Application No. 60/892,373, filed Mar. 1, 2007, and U.S. Provisional Patent Application No. 60/911,789, filed Apr. 13, 2007, where these two provisional applications are incorporated herein by reference in their entireties.

BACKGROUND

1. Technical Field

This application relates to salts of compounds that inhibit protein kinase activity, and to compositions, formulations and methods related to U.S. Provisional Patent Application No. 60/892,373, filed Mar. 1, 2007, and U.S. Provisional Patent Application No. 60/911,789, filed Apr. 13, 2007.

2. Description of Related Art

Cancer (and other hyperproliferative diseases) is characterized by uncontrolled cell proliferation. This loss of the normal control of cell proliferation often appears to occur as the result of genetic damage to cell pathways that control progress through the cell cycle. The cell cycle consists of DNA synthesis (S phase), cell division or mitosis (M phase), and non-synthetic periods referred to as gap 1 (G1) and gap 2 (G2). The M-phase is composed of mitosis and cytokinesis (separation into two cells). All steps in the cell cycle are controlled by an orderly cascade of protein phosphorylation and several families of protein kinases are involved in carrying out these phosphorylation steps. In addition, the activity of many protein kinases increases in human tumors compared to normal tissue and this increased activity can be due to many factors, including increased levels of a kinase or changes in expression of co-activators or inhibitory proteins.

Cells have proteins that govern the transition from one phase of the cell cycle to another. For example, the cyclins are a family of proteins whose concentrations increase and decrease throughout the cell cycle. The cyclins turn on, at the appropriate time, different cyclin-dependent protein kinases (CDKs) that phosphorylate substrates essential for progression through the cell cycle. Activity of specific CDKs at specific times is essential for both initiation and coordinated progress through the cell cycle. For example, CDK1 is the most prominent cell cycle regulator that orchestrates M-phase activities. However, a number of other mitotic protein kinases that participate in M-phase have been identified, which include members of the polo, aurora, and NIMA (Never-In-Mitosis-A) families and kinases implicated in mitotic checkpoints, mitotic exit, and cytokinesis.

Aurora kinases are a family of oncogenic serine/threonine kinases that localize to the mitotic apparatus (centrosome, poles of the bipolar spindle, or midbody) and regulate completion of centrosome separation, bipolar spindle assembly and chromosome segregation. Three human homologs of aurora kinases have been identified (aurora-1, aurora-2 and aurora-3). They all share a highly conserved catalytic domain located in the carboxyl terminus, but their amino terminal extensions are of variable lengths with no sequence similarity. The human aurora kinases are expressed in proliferating cells and are also overexpressed in numerous tumor cell lines including breast, ovary, prostate, pancreas, and colon. Aurora-2 kinase acts as an oncogene and transforms both Rat1 fibroblasts and mouse NIH3T3 cells in vitro, and aurora-2 transforms NIH 3T3 cells grown as tumors in nude mice. Excess aurora-2 may drive cells to aneuploidy (abnormal numbers of chromosomes) by accelerating the loss of tumor suppressor genes and/or amplifying oncogenes, events known to contribute to cellular transformation. Cells with excess aurora-2 may escape mitotic check points, which in turn can activate proto-oncogenes inappropriately. Up-regulation of aurora-2 has been demonstrated in a number of pancreatic cancer cell lines. In additional, aurora-2 kinase antisense oligonucleotide treatment has been shown to cause cell cycle arrest and increased apoptosis. Therefore, aurora-2 kinase is an attractive target for rational design of novel small molecule inhibitors for the treatment of cancer and other conditions.

c-Kit, also known as CD117, is a well-studied proto-oncogene encoding an oncogenic receptor tyrosine kinase. (Yarden, Y. et al., "Human proto-oncogene c-Kit: a new cell surface receptor tyrosine kinase for an unidentified ligand," *Embo J* 6:3341-51 (1987).) During receptor activation, the c-Kit ligand (stem cell factor, SCF or Steel factor) binds to the extracellular C2 immunoglobulin-like domains 1 through 3 of c-Kit and causes receptor homodimerization and trans-autophosphorylation which, in turn, leads to the activation of downstream signaling pathways and subsequent initiation of proliferation, survival, adhesion and chemotaxis, depending on environmental factors. (Blume-Jensen, P. et al., "Activation of the human c-Kit product by ligand-induced dimerization mediates circular actin reorganization and chemotaxis," *Embo J* 10:4121-8 (1991).)

Activating or gain-of-function mutations in the c-Kit proto-oncogene have been identified in a variety of tumors including gastrointestinal stromal tumors (GIST). (Heinrich, M. C., Blanke, C. D., Druker, B. J. & Corless, C. L., "Inhibition of KIT tyrosine kinase activity: a novel molecular approach to the treatment of KIT-positive malignancies," *J Clin Oncol* 20:1692-703 (2002); Hirota, S. et al., "Gain-of-function mutations of c-Kit in human gastrointestinal stromal tumors," *Science* 279:577-80 (1998); Frost, M. J., Ferrao, P. T., Hughes, T. P. & Ashman, L. K., "Juxtamembrane mutant V560GKit is more sensitive to Imatinib (STI571) compared with wild-type c-Kit whereas the kinase domain mutant D816VKit is resistant," *Mol Cancer Ther* 1:1115-24 (2002); Tian, Q., Frierson, H. F., Jr., Krystal, G. W. & Moskaluk, C. A., "Activating c-Kit gene mutations in human germ cell tumors," *Am J Pathol* 154:1643-47 (1999).) In GIST, the resulting constitutive c-Kit tyrosine kinase activity provides growth and survival advantages, which are important in the pathogenesis of this disease. (Heinrich, M. C., Rubin, B. P., Longley, B. J. & Fletcher, J. A., "Biology and genetic aspects of gastrointestinal stromal tumors: KIT activation and cytogenetic alterations," *Hum Pathol* 33:484-95 (2002).) c-Kit is validated as a critical target in GIST and while small molecule inhibitors can target c-Kit, such compounds are fraught with limitations. Imatinib mesylate, a potent inhibitor of c-Kit (Juurikivi, A. et al., "Inhibition of c-Kit tyrosine kinase by Imatinib mesylate induces apoptosis in mast cells in rheumatoid synovia: a potential approach to the treatment of arthritis," *Ann Rheum Dis* 64:1126-31 (2005)) is currently approved for the treatment of GIST. However, in some cases where c-Kit is known to be upregulated, imatinib has been shown to be ineffective (Alexis, J. B., Martinez, A. E. & Lutzky, J., "An immunohistochemical evaluation of c-Kit (CD-117) expression in malignant melanoma, and results of Imatinib mesylate (Gleevec) therapy in three patients," *Melanoma Res* 15:283-5 (2005)), possibly due to its inability to act against mutant forms of the c-Kit protein (Foster, R., Griffith, R., Ferrao, P. & Ashman, L., "Molecular basis of the constitutive activity and STI571 resistance of Asp816Val mutant KIT receptor tyrosine kinase," *J Mol Graph Model* 23:139-52 (2004); Growney, J. D. et al., "Activation mutations of human c-Kit resistant to Imatinib are sensitive to the tyrosine kinase inhibitor PKC412," *Blood* (2005); Gotlib, J. et al., "Activity of the tyrosine kinase inhibitor PKC412 in a patient with mast cell leukemia with the D816V KIT mutation," *Blood* (2005); Corbin, A. S. et al., "In vitro and in vivo activity of ATP-based kinase inhibitors AP23464 and AP23848 against activation-loop mutants of Kit," *Blood* 106:227-34 (2005)). To address this resistance, novel c-Kit inhibitors, with binding modes distinct from that of imatinib, might prove useful against mutant forms of the receptor.

PDGFRα is expressed in a wide variety of tissues, including kidney, testis, skin, intestine and lung epithelia, as well as in premature bone and muscle (Alvarez, R. H. et al., "Biology of platelet-derived growth factor and its involvement in disease," *Genetics in Clinical Practice* 81:1241-57 (2006)). It is a very common signaling molecule at all stages of development and is involved in the regulation of differentiation and proliferation, as many proliferative genes are (Alvarez et al., supra). However, the continued expression of this receptor in various epithelial and mesenchymal cells suggests that it is also involved in the maintenance and regeneration of these tissues (Alvarez et al., supra). Activation of this receptor leads to stimulation of PI-3K, Ras-MAPK, and PLC signaling cascades leading to growth, actin cytoskeleton rearrangements, and chemotaxis (Alvarez et al., supra). A subset of invasive gastric carcinomas (including some gastrointestinal stromal tumors, GISTs), pancreas cancer, gliomas and astrocytomas are associated with PDGFR dysregulation. A subset of GIST tumors have been shown to have mutations in PDGFRα, occurring in either exon 18 (5.6%) or exon 12 (1.2%) (Alvarez et al., supra). The most common mutation occurring in exon (Giorgi, U. D. et al., "Imatinib and gastrointestinal stromal tumors: Where do we go from here?," *Mol Cancer Ther* 4:495-501 (2005)) is the point mutation D842V and in exon 12 it is the point mutation V561 D (Corless, C. L. et al., "PDGFRA mutations in gastrointestinal stromal tumors: frequency, spectrum and in vitro sensitivity to Imatinib," *J Clin Onco* 23:5357-5364 (2005); Giorgi et al., supra). Both are activating mutations in vitro and interestingly, GIST tumors expressing mutated PDGFRα have not been shown to express mutant c-Kit (Alvarez et al., supra; Corless et al., supra; Giorgi et al., supra). The D842V mutant PDGFRα has been correlated with resistance to imatinib treatment. Based on these data, compounds that inhibit the D842V PDGFRαmutant may have activity in these resistant forms of GIST (Corless et al., supra).

Similar to c-Kit and PDGFR, Flt3 (Fms-like tyrosine kinase 3, FLk-2, or STK-1) is a member of the class III receptor tyrosine kinase family. Flt3 expression is seen predominantly in early CD34+ hematopoietic progenitor cells (Advani, A. S., "FLT3 and acute myelogenous leukemia: biology, clinical significance and therapeutic applications," *Cur Pharm Des* 11:3449-57 (2005); Schmidt-Arras, D. et al., "Flt3 receptor tyrosine kinase as a drug target in leukemia," *Cur Pharm Des* 10:1867-83 (2004)). The ligand for Flt3, Flt3 ligand (FL), is expressed in bone marrow stromal cells in either membrane-bound or soluble forms (Advani, supra; Schmidt-Arras et al., supra). Activation of Flt3 by FL initiates signal cascades that are essential in the proliferation, differentiation, and survival of normal hematopoietic progenitor cells (Advani, supra; Schmidt-Arras et al., supra). Two key downstream effectors of Flt3, PI-3K and Ras, initiate signaling cascades that stimulate cellular proliferation and cell survival (Advani, supra; Schmidt-Arras et al., supra). Mutations of Flt3 that over-express or constitutively activate the kinase, cause dysregulation of these downstream signaling cascades and may lead to leukemia. The most commonly identified mutations in AML are internal tandem duplications (ITD) of the juxtamembrane domain and point mutations of Asp835 (Advani, supra). Substitution of Asp835 with tyrosine, valine, histidine, glutamic acid, and aspargine have all been described with the D835Y substitution being the most common (Advani, supra; Schmidt-Arras et al., supra). Point mutations at D835 occur in the activation loop of the tyrosine kinase domain and cause the kinase to adapt an active configuration in the absence of ligand stimulation (Advani, supra). The prevalence of point mutations at D835 is: 7% in AML, 3% in MDS, and 3% in ALL (Schmidt-Arras et al., supra).

DNA repair pathways initiated in response to DNA damage utilize a protein called RAD51 which has been shown to be critical to the repair process in non-cancerous cells, but can be used as a mechanism of resistance to DNA-damaging agents in tumor cells. A correlation between the expression of high levels of RAD51 and resistance to chemotherapeutic drugs has been reported (Qiao, G-B, et al., "High-level expression of RAD51 is an independent prognostic marker of survival in non-small-cell lung cancer patients," *Brit J Cancer* 93:137-43 (2005); Hansen, L. T. et al., "The role of RAD51 in Etoposide (VP16) resistance in small cell lung cancer," *Int J Cancer* 105:472-79 (2003); Henning, W. et al., "Homologous recombination and cell cycle checkpoints: RAD51 in tumour progression and therapy resistance," *Toxicology* 193:91-109 (2003)). Additionally, decreasing levels of RAD51 in cells increases their sensitivity to ionizing radiation (IR).

MP470 (4-[1]benzofuro[3,2-d]pyrimidin-4-yl-N-(1,3-benzodioxol-5-ylmethyl)piperazine-1-carbothioamide hydrochloride) (e.g., WO2005/037825) has demonstrated inhibitory activity against multiple protein kinases, including Aurora kinase, c-kit kinase and PDGFRα. In light of its potent anticancer activity, there is a need for identifying effective formulations of MP470 for clinical use. There is also a need for identifying other therapies or treatment modalities that can be effectively used in combination with formulations comprising MP470. The present invention addresses these needs and offers other related advantages.

BRIEF SUMMARY OF THE INVENTION

According to the present invention, pharmaceutical formulations comprising salt forms of MP470 are provided. Such formulations offer decreased toxicity and increased oral bioavailability relative to the free base form of MP470.

In one embodiment, the salt of MP470 is synthesized with an acid, optionally with an acid having a pKa of about 5 or less, optionally with an acid having pKa of about 4 or less, optionally with an acid having pKa ranging from about 3 to about 0, or optionally with an acid having pKa ranging from about 3 to about −10.

Preferably, the acid is selected from the group consisting of hydrochloric, L-lactic, acetic, phosphoric, (+)-L-tartaric, citric, propionic, butyric, hexanoic, L-aspartic, L-glutamic, succinic, EDTA, maleic, HBr, HF, HI, nitric, nitrous, sulfuric, sulfurous, phosphorous, perchloric, chloric, chlorous acid, carboxylic acid, sulfonic acid, ascorbic, carbonic, and fumaric acid. In particular, the sulfonic acid is selected from the group consisting of methanesulfonic acid, ethanesulfonic, 2-hydroxyethanesulfonic, and toluenesulfonic acid.

In another embodiment, a salt of MP470 is provided. The salt of MP470 is selected from the group consisting of hydrochloride, L-lactate, acetate, phosphate, (+)-L-Tartrate, citrate, propionate, butyrate, hexanoate, L-aspartate, L-glutamate, succinate, EDTacetate, mesylate, maleate, hydrobromide, hydrofluoride, hydroiodide, nitrate, nitrite, sulfate, sulfite, phosphate, perchlorate, chlorate, chlorite, carboxylate, sulfonate, ascorbate, carbonate, esylate, tosylate, and fumarate. In particular, the sulfonate is selected from the group consisting of methanesulfonate, ethanesulfonate, 2-hydroxyethanesulfonate, and toluenesulfonate acid. In a preferred embodiment, the salt of MP470 is selected from the group consisting of hydrochloride, acetate, phosphate, mesylate, esylate, tosylate, and nitrate.

In one embodiment, the salt of MP470 is hydrochloride salt in crystalline form characterized by an X-ray diffraction pattern having diffraction peaks (2θ) at 8.1°, 13.0°, and 24.6°. The salt is further characterized by a melting endotherm of 180-210° C., optionally 185-200° C., as measured by differential scanning calorimetry at a scan rate of 10° C. per minute.

In another embodiment, the salt of MP470 is a hydrochloride salt in crystalline form characterized by an X-ray diffraction pattern having diffraction peaks (2θ) at 9.5°, 10.4°, 11.4°, 14.1°, and 25.5°.

In another aspect of the invention, pharmaceutical formulations are provided which comprise a salt of MP470 with pharmaceutically acceptable excipients. In a particular embodiment, the pharmaceutical formulation of the salt of MP470 is delivered orally.

Also according to the present invention, a method is provided for treating a disease associated with undesirable cell proliferation in a subject. The method comprises administering to the subject in need thereof a pharmaceutically effective amount of a formulation comprising a salt of MP470. The disease may be benign tumors, cancer, hematological disorders, atherosclerosis, insults to body tissue due to surgery, abnormal wound healing, abnormal angiogenesis, diseases that produce fibrosis of tissue, repetitive motion disorders, disorders of tissues that are not highly vascularized, or proliferative responses associated with organ transplants. Preferably, the disease is glioblastoma multiforme, ovarian cancer, gastro intestinal stromal tumors, non-small cell lung cancer, or medullary or papillary thyroid carcinoma.

In another aspect of the present invention, a method is provided for treating a disease associated with undesirable cell proliferation in a subject in which a formulation comprising a salt of MP470 is delivered in combination with a DNA damaging agent, wherein the DNA damaging agent may be selected, for example, from the group consisting of gamma radiation; platinums, such as cisplatin, carboplatin, satraplatin, and oxaliplatin; topoisomerase I inhibitors, such as camptothecin, irinotecan, and topotecan; and topoisomerase II inhibitors, such as etoposide and teniposide.

The present invention also provides methods for synthesizing, formulating and manufacturing salts of a cytidine analog.

DETAILED DESCRIPTION OF THE PRESENT INVENTION

Figure 1:
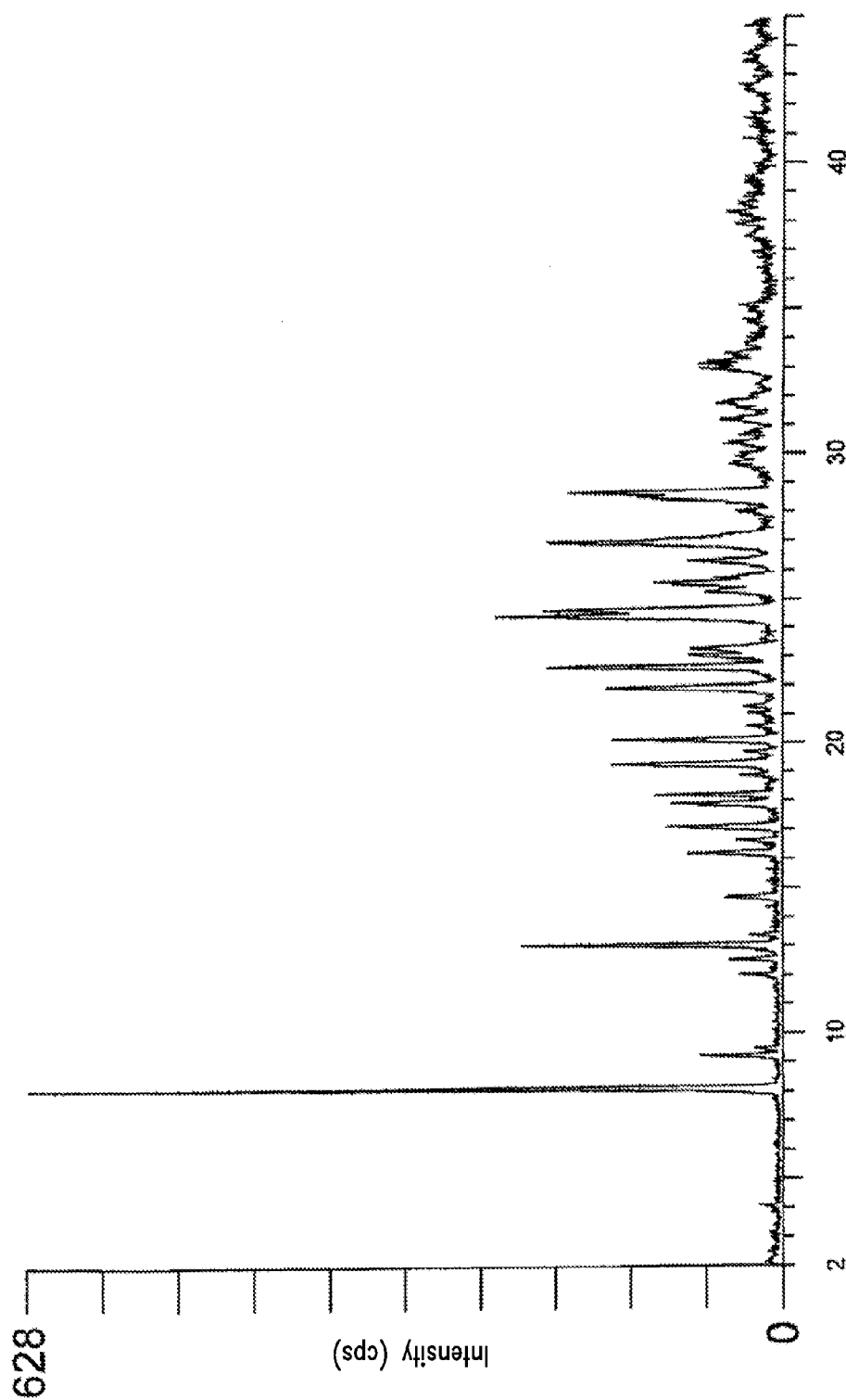
FIG. 1 illustrates a XRD pattern of one form of MP470 hydrochloride.

The present invention provides salts of a protein kinase inhibitor, specifically, MP470, which can be used in pharmaceutical formulations for the treatment of various diseases and conditions that are sensitive to treatment with protein kinase inhibitors. Certain formulations of the invention overcome the poor oral bioavailability of MP470 free base and the poor tolerability of an intravenous formulation of MP470 free base.

According to the present invention, the solid state and solution properties of MP470 are modified by salt formation. The modified properties enable the salt to pass through the gastrointestinal barrier and reach the vascular environment. In certain embodiments, the salt of MP470 improves the oral drug availability 10-fold over that of the free base.

Increased water-solubility can also potentially make the drug entities less toxic. Due to their easier renal clearance they are less likely to accumulate and overload the hepatic microsomes responsible for phase-one and phase-two metabolism.

In other embodiments, salts of MP470 also improve the tolerability of the drug when delivered orally in comparison to the tolerability of the free base delivered via the intravenous route.

The salts of MP470 can be formulated in various ways and delivered to a patient suffering from a disease sensitive to the treatment with MP470 via various routes of administration such as intravenous, intramuscular, subcutaneous injection and inhalation. In a preferred embodiment, the salt of MP470 is in a formulation suitable for oral administration.

The present invention also provides methods for synthesizing, formulating and manufacturing salts of cytidine analogs, and methods for using the salts for treating various diseases and conditions.

The salts of MP470 and formulations comprising same can be used to treat indications that involve undesirable or uncontrolled cell proliferation. Such indications include, for example, benign tumors, various types of cancers such as primary tumors and tumor metastasis, restenosis (e.g., coronary, carotid, and cerebral lesions), hematological disorders, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Certain preferred indications for treatment with MP470 salts include, but are not limited to glioblastoma multiforme, ovarian cancer, gastro intestinal stromal tumors, non-small cell lung cancer, or medullary or papillary thyroid carcinoma.

The following is a detailed description of the invention and certain preferred embodiments of the inventive salts, formulations, compositions and methods of use.

Salts of MP470

One aspect of the invention provides salt forms of MP470 (1), a carbothioamide, whose structure is depicted below:

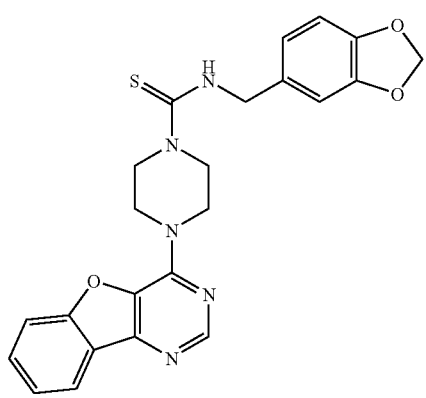

(1)

In some embodiments, to ensure sufficient proton transfer from the acid to a basic drug, the newly formed conjugate acid and conjugate base should be weaker than the original acid and basic drug, generally by at least about 2 units weaker than the $pK_a$ of the drug. The $pK_a$ of MP470 was found to be 6.7. In preferred embodiments, an acid with $pK_a$ lower than about 5, or optionally with $pK_a$ between 3 and −10, is used to synthesize a salt form of MP470. Illustrative, but not limiting, examples of suitable acids are listed in Table 1.

TABLE 1

Examples of acids that can be used to synthesize a salt form of MP470

| Name | $pK_{a1}$ | $pK_{a2}$ | Name | $pK_{a1}$ | $pK_{a2}$ |
|---|---|---|---|---|---|
| Perchloric acid | −10 | — | Fumaric acid | 3.03 | 4.38 |
| Hydrobromic acid | −9 | — | Galactaric acid | 3.08 | 3.63 |
| Hydroiodic acid | −9 | — | Hydrofluoric acid | 3.16 | — |
| Hydrochloric acid | −6 | — | Citric acid | 3.13 | 4.76 |
| Naphthalene-1,5-disulfonic acid | −3.37 | −2.64 | D-Glucuronic acid | 3.18 | — |
| Sulfuric acid | −3 | 1.92 | Lactobionic acid | 3.2 | — |
| Ethane-1,2-disulfonic acid | −2.1 | −1.5 | 4-Amino-salicylic acid | 3.25 | 10 |
| Cyclamic acid | −2.01 | — | Glycolic acid | 3.28 | — |
| p-Toluenesulfonic acid | −1.34 | — | D-Glucoheptonic acid | 3.3 | — |
| Thiocyanic acid | −1.33 | — | Nitrous acid | 3.3 | — |
| Nitric acid | −1.32 | — | (−)-L-Pyroglutamic acid | 3.32 | — |
| Methanesulfonic acid | −1.2 | — | DL-Mandelic acid | 3.37 | — |
| Chloric acid | −1.0 | — | (−)-L-Malic acid | 3.46 | 5.10 |
| Chromic acid | −0.98 | 6.50 | Hippuric acid | 3.55 | — |
| Dodecylsulfuric acid | −0.09 | — | Formic acid | 3.75 | — |
| Trichloroacetic acid | 0.52 | — | D-Gluconic acid | 3.76 | — |

TABLE 1-continued

Examples of acids that can be used to synthesize a salt form of MP470

| Name | $pK_{a1}$ | $pK_{a2}$ | Name | $pK_{a1}$ | $pK_{a2}$ |
|---|---|---|---|---|---|
| Benzenesulfonic acid | 0.7 | — | DL-Lactic acid | 3.86 | — |
| Iodic | 0.80 | — | Oleic acid | 4 | — |
| Oxalic acid | 1.27 | 4.27 | L-Ascorbic acid | 4.17 | 11.57 |
| 2,2-Dichloro-acetic acid | 1.35 | — | Benzoic acid | 4.19 | — |
| Glycerophosphoric acid | 1.47 | — | Succinic acid | 4.21 | 5.64 |
| 2-Hydroxy-ethanesulfonic acid | 1.66 | — | 4-Acetamido-benzoic acid | 4.3 | — |
| EDTA | 1.70 | 2.60 | Glutaric acid | 4.34 | 5.27 |
| Phosphorous acid | 1.80 | 6.15 | Cinnamic acid | 4.40 | — |
| Sulfurous | 1.85 | 7.20 | Adipic acid | 4.44 | 5.44 |
| L-Aspartic | 1.88 | 3.65 | Sebacic acid | 4.59 | 5.59 |
| Maleic acid | 1.92 | 6.23 | (+)-Camphoric acid | 4.72 | 5.83 |
| Phosphoric acid | 1.96 | 7.12 | Acetic acid | 4.76 | — |
| Chlorous acid | 1.98 | — | Hexanoic acid | 4.8 | — |
| Ethanesulfonic acid | 2.05 | — | Butyric acid | 4.83 | — |
| (+)-Camphor-10-sulfonic acid | 2.17 | — | Nicotinic acid | 4.85 | — |
| Glutamic acid | 2.19 | 4.25 | Isobutyric acid | 4.86 | — |
| Alginic acid | >2.4 | — | Propionic acid | 4.87 | — |
| Pamoic acid | 2.51 | — | Decanoic acid | 4.9 | — |
| Glutaric acid | 2.7 | — | Lauric acid | 4.9 | — |
| 1-Hydroxy-2-naphthoic acid | 2.7 | — | Palmitic acid | 4.9 | — |
| Malonic acid | 2.83 | — | Stearic acid | 4.9 | — |
| Gentisic acid | 2.93 | — | Undecylenic acid | 4.9 | — |
| Salicylic acid | 2.97 | — | Octanoic acid | 4.91 | — |
| (+)-L-Tartaric acid | 3.02 | 4.36 | Malic acid | 5.05 | — |

In certain preferred embodiments, MP470 salts are formed with strong acids ($pK_a<0$).

Certain embodiments of the invention provide salt forms of MP470 synthesized with an acid. For example, certain embodiments include salt forms synthesized with the following acids —HCl, L-lactic, acetic, phosphoric, (+)-L-tartaric, citric, propionic, butyric, hexanoic, L-aspartic, L-glutamic, succinic, EDTA, maleic, and methanesulfonic. Other embodiments include MP470 salts of other common acids. Examples of suitable inorganic acids include, but are not limited to, HBr, HF, HI, nitric, nitrous, sulfuric, sulfurous, phosphorous, perchloric, chloric, and chlorous acid. Examples of suitable carboxylic acids include, but are not limited to, ascorbic, carbonic, and fumaric acid. Examples of suitable sulfonic acids include, but are not limited to, ethanesulfonic, 2-hydroxyethanesulfonic, and toluenesulfonic acid.

Preferably, the molar ratios of acids to MP470 are about 0.01 to about 10 molar equivalents. Preferred embodiments include MP470 salts of strong acids (pKa<0). More preferred embodiments include MP470 hydrochloride (2) illustrated below, which can form in 1:1 molar equivalent (e.g., as determined from elemental analysis).

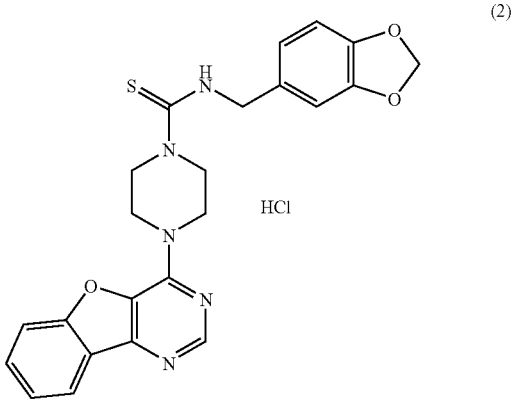

(2)

Pharmaceutical Formulations of the Present Invention

According to the present invention, the salts of MP470 can be formulated into pharmaceutically acceptable compositions/formulations for treating various diseases and conditions.

The pharmaceutically-acceptable compositions and formulations of the present invention comprise one or more salts of the invention in association with one or more nontoxic, pharmaceutically-acceptable carriers and/or diluents and/or adjuvants and/or excipients, collectively referred to herein as "carrier" materials, and if desired other active ingredients.

The salts of the present invention are administered by any route, preferably in the form of a pharmaceutical formulation adapted to such a route, as illustrated below and are dependent on the condition being treated. The compounds and formulations can be, for example, administered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by a catheter or stent), subcutaneously, intraadiposally, intraarticularly, or intrathecally. In a preferred embodiment of the present invention, the salts of MP470 are administered as a pharmaceutical formulation via the peroral route.

The pharmaceutical formulation may optionally further include an excipient added in an amount sufficient to enhance the stability of the composition, maintain the product in solution, or prevent side effects (e.g., potential ulceration, vascular irritation or extravasation) associated with the administration of the inventive formulation. Examples of excipients include, but are not limited to, mannitol, sorbitol, lactose, dextrose, cyclodextrin such as, α-, β-, and γ-cyclodextrin, and modified, amorphous cyclodextrin such as hydroxypropyl-, hydroxyethyl-, glucosyl-, maltosyl-, maltotriosyl-, carboxyamidomethyl-, carboxymethyl-, sulfobutylether-, and diethylamino-substituted α-, β-, and γ-cyclodextrin. Cyclodextrins such as Encapsin® from Janssen Pharmaceuticals or equivalent may be used for this purpose.

For oral administration, the pharmaceutical formulation can be in the form of, for example, a tablet, capsule, suspension or liquid. The pharmaceutical formulation is preferably made in the form of a dosage unit containing a therapeutically-effective amount of the active ingredient. Examples of such dosage units are tablets and capsules. For therapeutic purposes, the tablets and capsules can contain, in addition to the active ingredient, conventional carriers such as surfactants, for example, sodium lauryl sulfate, sodium docusate; binding agents, for example, acacia gum, gelatin, polyvinylpyrrolidone, sorbitol, or tragacanth; fillers, for example, micro crystalline cellulose, calcium phosphate, glycine, lactose, maize-starch, sorbitol, or sucrose; lubricants, for example, magnesium stearate, polyethylene glycol, colloidal silicon dioxide, or talc; disintegrants, for example, potato starch, flavoring or coloring agents, or acceptable wetting agents. Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For topical use the salts of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the salts of the present invention can be presented in liquid or semi-liquid form formulated in hydrophobic or hydrophilic bases as ointments, creams, lotions, paints or powders.

For rectal administration the salts of the present invention can be administered in the form of suppositories admixed with conventional carriers such as cocoa butter, wax or other glyceride.

Alternatively, the salts of the present invention can be in powder form for reconstitution in the appropriate pharmaceutically acceptable carrier at the time of delivery.

The pharmaceutical formulations can be administered via injection. Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The salts can be dissolved in water, polyethylene glycol, propylene glycol, ethanol, corn oil, benzyl alcohol, sodium chloride, and/or various buffers.

In one embodiment, the salt of the present invention can be formulated into a pharmaceutically acceptable composition comprising the compound solvated in non-aqueous solvent that includes glycerin, propylene glycol, polyethylene glycol, or combinations thereof.

Indications for Inventive Salts or Formulations Thereof

The inventive salts/formulations described herein have many therapeutic and prophylactic uses. In a preferred embodiment, the salt forms of MP470 are used in the treatment of a wide variety of diseases that are sensitive to the treatment with protein kinase inhibitors. Certain indications that may be treated using the inventive salts/formulations include those involving undesirable or uncontrolled cell proliferation. Such indications include benign tumors, various types of cancers such as primary tumors and tumor metastasis, restenosis (e.g., coronary, carotid, and cerebral lesions), hematological disorders, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Generally, cells in a benign tumor retain their differentiated features and do not divide in a completely uncontrolled manner. A benign tumor is usually localized and nonmetastatic. Specific types benign tumors that can be treated using the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a malignant tumor cells become undifferentiated, do not respond to the body's growth control signals, and multiply in an uncontrolled manner. The malignant tumor often becomes invasive and capable of spreading to distant sites (metastasizing). Malignant tumors are generally divided into two categories: primary and secondary. Primary tumors arise directly from the tissue in which they are found. A secondary tumor, or metastasis, is a tumor which is originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.)

Specific types of cancers or malignant tumors, either primary or secondary, that can be treated using this invention include breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Hematologic disorders include abnormal growth of blood cells which can lead to dysplastic changes in blood cells and hematologic malignancies such as various leukemias. Examples of hematologic disorders include but are not limited to acute myeloid leukemia, acute promyelocytic leukemia, acute lymphoblastic leukemia, chronic myelogenous leukemia, the myelodysplastic syndromes, and sickle cell anemia.

The present invention also provides methods treating a disease associated with undesirable cell proliferation in a subject in which a salt of MP470 is delivered in combination with a DNA damaging agent, wherein the DNA damaging agent may be, for example, gamma radiation or platinums, such as cisplatin, carboplatin, satraplatin, and oxaliplatin.

EXAMPLES

The following examples are intended to illustrate details of the invention, without thereby limiting it in any manner.

An example procedure to synthesize a salt of a free base is described. Dissolve the organic base in a minimal amount of heated solvent, typically selected from a group consisting of methanol, ethanol, isopropanol, acetone, and ethylene oxide. Add calculated volume of concentrated acid. If, after cooling, crystallization does not occur, precipitation is initiated by adding more solvent or reducing the volume of the mixture.

Synthesis of MP470 Salts

MP470 Hydrochloride Salt Formation

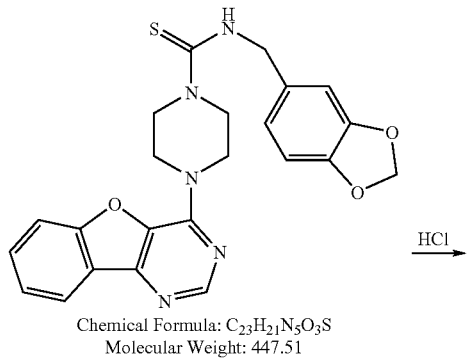

Chemical Formula: $C_{23}H_{21}N_5O_3S$
Molecular Weight: 447.51

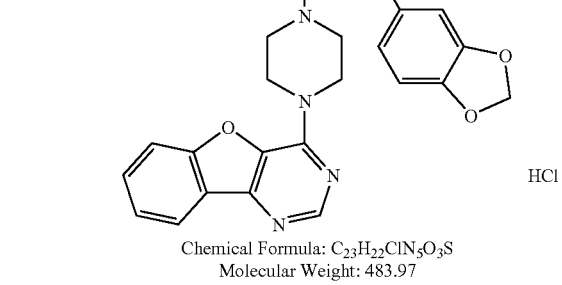

Chemical Formula: $C_{23}H_{22}ClN_5O_3S$
Molecular Weight: 483.97

3 g (6.7 mmol) of MP470 was dissolved into 2.8 L of acetone in a flask with gentle heating. The solution was then cooled to room temperature and filtered. Next, 0.55 ml (6.7 mmol) of concentrated HCl (37% w/v) was added to the filtrate. The flask was left in the chemical hood covered with a tissue wiper. After 2 hours crystals slowly began to form on the flask wall. After 3 days the solid was filtered and dried under vacuum to give 3.0 g MP470HCl salt (yield 92%).

MP-470 (100 mg, 0.223 mmol) was dissolved into 80 mL of acetone in flask with gentle heating. The solution was cooled down to room temperature and filtered. To the filtrate was added 0.018 mL (0.223 mmol) of concentrated HCl (37% w/w). The flask was shaken gently for 10 seconds, then it was left in hood with tissue wipers covered. A couple of hours later, crystals formed slowly on flask wall. Overnight, filtration and dry the solid under vacuum to give MP470HCl salt: 66 mg (yield 61%).

MP-470 (1 g, 2.23 mmol)) was dissolved into 900 mL of acetone in flask with gentle heating. The solution was cooled down to room temperature and filtered. To the filtrate was added 0.18 mL (2.23 mmol) of concentrated HCl (37% w/w). The flask was shaken gently for 10 seconds, then it was left in hood with tissue wipers covered. A couple of hours later, crystals formed slowly on flask wall. Overnight, the solvent was evaporated slowly to 600 mL with N2. On the following day's morning, the solid was filtered and dried under vacuum to give MP470HCl salt: 822 mg (yield 76%).

MP-470 (3 g, 6.7 mmol) was dissolved into 2.7 L of acetone in flask with gentle heating. The solution was cooled down to room temperature and filtered. To the filtrate was added 0.55 mL (6.7 mmol) of concentrated HCl (37% w/w) with stirring. White precipitate formed quickly. The flask was left without stirring in hood with tissue wipers covered. Overnight, the solid was filtered and dried under vacuum to give MP470HCl salt: 2.74 g (yield 84%).

MP-470 (3 g, 6.7 mmol)) was dissolved into 2.7 L of acetone in flask with gentle heating. The solution was cooled down to room temperature and filtered. To the filtrate was added 0.55 mL (6.7 mmol) of concentrated HCl (37% w/w). The flask was left without stirring in hood with tissue wipers covered. A couple of hours later, crystals formed slowly on flask wall. Overnight, a stirbar was added and the mixture was stirred for 0.5 h. The mixture was left in hood overnight. The solid was filtered and dried under vacuum to give MP-470HCl salt: 2.84 g (yield 87%).

MP-470 (3 g, 6.7 mmol)) was dissolved into 2.8 L of acetone in flask with gentle heating. The solution was cooled down to room temperature and filtered. To the filtrate was added 0.55 mL (6.7 mmol) of concentrated HCl (37% w/w). The flask was left in hood with tissue wiper covered. A couple of hours later, crystals formed slowly on flask wall. 3 days later, the solid was filtered and dried under vacuum to give MP-470HCl salt: 3.0 g (yield 92%).

A 100 mL 3-neck round bottom flask was equipped with a Claisen adapter, temperature probe, J-Kem controller, a chiller-cooled condenser, and a magnetic stir bar. One gram (1.0 g) of MP-470 was added to the flask followed by 20 mL 95% ethanol. The suspension was warmed to 72° C. with stirring. No dissolution of the solid occurred at reflux. One milliliter (5.3 equivalents) of concentrated HCl was measured and added in a drop wise manner to the refluxing suspension via a disposable glass pipette. The MP-470 suspension clarified during the first ½ mL addition, but an abundant pale yellow suspension formed during the addition of the last ½ mL conc. HCl. The reaction heat was discontinued and the suspension was left stirring overnight with the heating mantle in place. The suspension was vacuum filtered through Whatman 54 filter paper. The flask and filter cake was washed 3×~15 mL chilled ethanol. The MP-470HCl salt was dried in a vacuum oven (house vacuum) at 44-45° C. overnight to give MP-470HCl salt: 1.04 g (yield 94%).

A 100 mL 3-neck round bottom flask was equipped with a Claisen adapter and a magnetic stir bar. One gram (1.0 g) of MP-470 was added to the flask followed by 20 mL 95% ethanol. The suspension was stirred at room temperature (22° C.). One milliliter (5.3 equivalents) of concentrated HCl was measured and added in a drop wise manner to the refluxing suspension via a disposable glass pipette. Conc. HCl was added in two portions of ½ mL. The suspension was stirred for 4 days before it was vacuum filtered through Whatman 54 filter paper. The flask and filter cake was washed 3×~15 mL chilled ethanol. The MP-470HCl salt was dried in a vacuum oven (house vacuum) at 44-45° C. overnight to give MP-470HCl salt: 1.0 g (yield 92%).

A one-liter round bottom 3-neck flask was equipped with a magnetic stir bar and a 25-milliliter addition funnel. Twenty grams of MP-470 and 400 milliliters of 95% ethanol were added to the flask. The suspension was stirred as conc. HCl volume was slowly added (20 milliliters total, 5.3 equivalents). The duration of the addition was approximately 15 minutes. Following addition, the suspension was stirred for 2 hours before filtering through double-stacked Whatman 1 filter paper. The filter cake was dried in a vacuum oven (house vacuum) at 44-45° C. overnight to give MP-470HCl salt: 21.3 g (yield 99%).

A 5-liter 3-neck round bottom flask was equipped with a mechanical stirrer, temperature probe, J-Kem controller, and a 50 mL addition funnel. MP-470 (203.5 g) was charged to the reactor along with 4 L 95% ethanol. The suspension was stirred and warmed to 30° C. (+/−2° C.). Fifty milliliters of conc. HCl was added to the addition funnel. A fifty percent volume of concentrated HCl (25 ml, 0.55 equiv.) was added over a 3-minute period. Following determination of pH stability, the second 25 mL of conc. HCl (0.55 equiv.) was added over 3 min. The resulting suspension was vacuum filtered through double layer Whatman 1 filter paper. The filter cake was then transferred to a tray for drying at 51° C. and 5-8 mBar vacuum for 3 days to give MP-470HCl salt: 216 g (98% yield).

All MP-470HCl salt samples prepared by the protocol described above were analyzed by elemental analysis for C, H, N, and Cl, and results were within 0.4% of theory.

Using a similar synthetic procedure as used for the MP470HCl salt, MP470 mesylate (3), MP470 sulfate (4), MP470 esylate (5), MP470 besylate (6), MP470 tosylate (7), MP470 phosphate (8), and MP470 nitrate (9) were also synthesized.

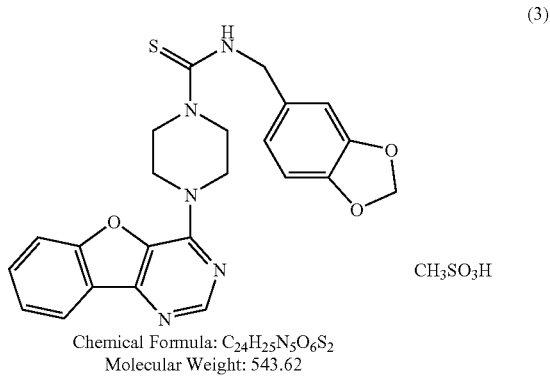

(3)

Chemical Formula: $C_{24}H_{25}N_5O_6S_2$
Molecular Weight: 543.62

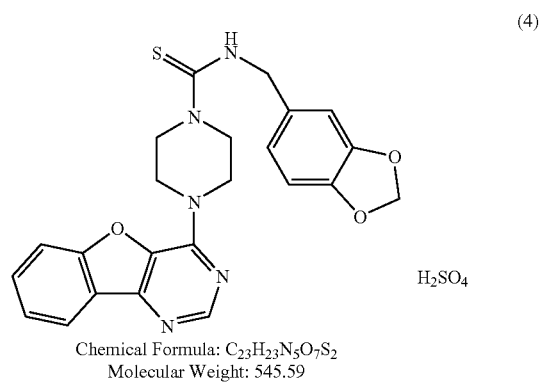

(4)

Chemical Formula: $C_{23}H_{23}N_5O_7S_2$
Molecular Weight: 545.59

-continued

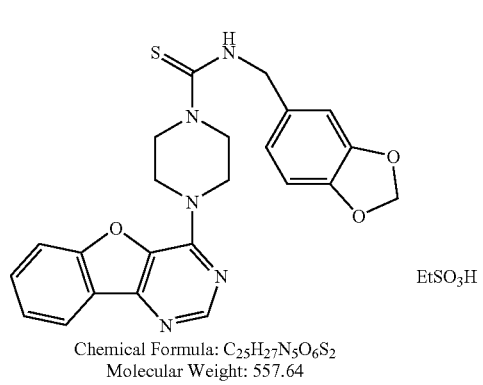

Chemical Formula: C$_{25}$H$_{27}$N$_5$O$_6$S$_2$
Molecular Weight: 557.64

EtSO$_3$H (5)

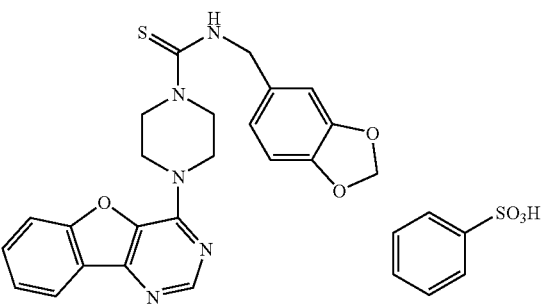

Chemical Formula: C$_{29}$H$_{27}$N$_5$O$_6$S$_2$
Molecular Weight: 605.68

(6)

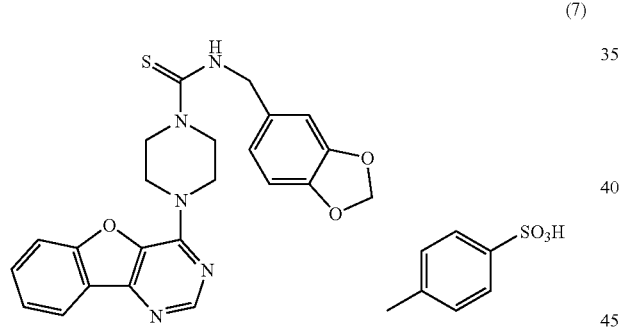

Chemical Formula: C$_{30}$H$_{29}$N$_5$O$_6$S$_2$
Molecular Weight: 619.71

(7)

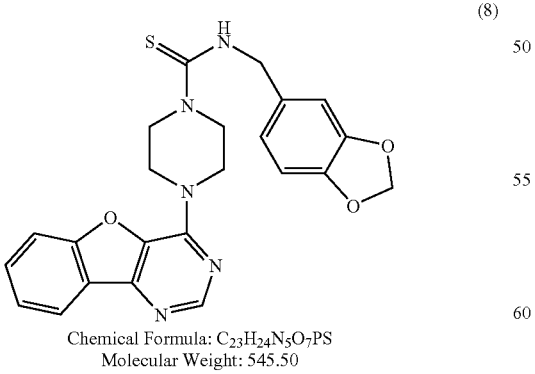

Chemical Formula: C$_{23}$H$_{24}$N$_5$O$_7$PS
Molecular Weight: 545.50

(8)

-continued

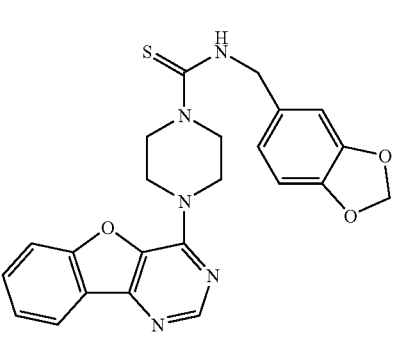

Chemical Formula: C$_{23}$H$_{22}$N$_6$O$_6$S
Molecular Weight: 510.52

(9)

Table 2 lists the properties of the MP470 salts described above.

TABLE 2

| Properties of MP470 salts | | | | |
|---|---|---|---|---|
| Properties | MP470 | MP470 Mesylate | MP470 HCl Salt | MP470 Sulfate |
| M.W. | 447.51 | 543.61 | 483.97 | 545.59 |
| m.p. | 194~195° C. | 209~210° C. | 211~212° C. | 229.5~230.5° C. |
| $^1$H-NMR (DMSO) | 4.07 (dd, $J_1$ = 17.8 Hz, $J_2$ = 5.81 Hz, 8H, NCH$_2$CH$_2$N) 8.55 (s, 1H, NCHN) | 2.29 (s, 3H, CH$_3$SO$_3$), 4.08 (d, J = 5.37, 4H, NCH$_2$), 4.19 (br-s, 4H, N$^+$CH$_2$), 8.72 (s, 1H, NCHN) | 4.08 (d, J = 3.08 Hz, 4H, NCH$_2$), 4.17 (d, J = 4.87 Hz, 4H, N$^+$CH$_2$), 8.706 (s, 1H, NCHN) | 4.088 (t, J = 4.1 Hz, 4H, NCH2), 4.226 (br-s, 4H, N$^+$CH$_2$), 8.791 (s, 1H, NCHN) |
| $^{13}$C-NMR, DEPT (DMSO) | CH$_2$ peaks: 100.738, 48.198, 46.778, 44.221 | CH$_2$ peaks: 100.752, 48.212, 46.286, 45.036 | | |
| Solubility (50 mM PBS buffer, pH 7, Exp. 15) | 1.22 µg/mL | 2.16 µg/mL | 3.28 µg/mL | 1.70 µg/Ml |
| Solubility in water | 4.94 µg/mL | 5.96 µg/mL | 31.14 µg/mL | 3.30 µg/mL |
| Elemental analysis (Quantitative Technologies Inc.) | Calcd: C: 61.73 H: 4.73 N: 15.65 S: 7.17 Found: C: 61.52 H: 4.64 N: 15.59 S 7.22 | | Calcd: C: 57.08 H: 4.58 N: 14.47 S: 6.63 Cl: 7.33 Found: C: 57.19 H: 4.46 N: 14.24 S: 6.52 Cl: 7.14 | |
| Properties | MP470 Esylate | MP470 Besylate | MP470 Tosylate | MP470 Nitrate |
| M.W | 557.64 | 605.69 | 637.71 | 510.52 |
| m.p | 205~6° C. | 189~90° C. | 210~2° C. | 212~3° C. |
| $^1$H-NMR | 1.05 (t, J = 7.5 Hz), 2.39 (q, J = 6.5 Hz), 4.15 (br-s, 4H), 4.08 (m, 4H), 8.74 (s, 1H) | 4.08 (m, 1H), 4.17 (m, 4H), 7.29 (m, 3H, Ben), 7.5 (m, 2H, Ben) | 2.27 (s, 3H), 4.08 (m, 4H), 4.20 (m, 4H), 7.09 (d, J = 7.9 Hz, 2H), 7.45 (d, J = 8.2 Hz, 2H), 8.74 (s, 1H) | 4.19 (m, 4H), 4.08 (m, 4H), 8.73 (s, 1H) |
| Solubility in H$_2$O | 5.89 µg/mL | 4.26 µg/mL | 1.87 µg/mL | 11.16 µg/mL |

Unexpectedly, MP470 salts displayed very little, if any, improvement in solubility over the free base form. The solubility of MP470.HCl in several common solvents at room temperature (RT) is summarized in Table 3.

TABLE 3

Solubility of MP470•HCl in Common Solvents

| Solvent | Solubility (mg/mL) |
|---|---|
| Water | <detectable limit by HPLC |
| Methanol | 3 |
| Ethanol | 0.4 |
| Benzyl alcohol | 48 |
| DMSO | 17 |
| DMF | 9 |
| Propylene glycol | 4 |
| Glycerol | 4 |

Dissociation constants (pKa) were obtained using a mixed-solvent method and determined by pH to be 6.81, 7.09 and 7.10, respectively, using three semi-aqueous solutions of MP470 in 30, 60 and 90% (v/v) methanol, respectively. The apparent pKa in aqueous solution was extrapolated from the determined pKa values (the apparent ionization constants in methanol-water solvent) plotted versus the percent methanol used. The apparent pKa of MP470 was determined to be 6.7.

The log P value for MP470 was determined by the traditional shake-flask method with octanol/water partitioning. Citrate buffer at pH 2 was the aqueous phase. The concentration of the solute in the organic phase was analyzed by HPLC analysis of MP470 with respect to a calibration curve ranging from 0.2 to 200 µg/mL MP470. The majority of MP470 was found in the organic phase. The log P value of MP470 was determined to be 2.3.

The ultraviolet absorbance spectrum of MP470.HCl in methanol displays four maxima (Table 4).

TABLE 4

| UV Maxima for MP470•HCl | |
|---|---|
| λ-max (nm) | $\epsilon$ (cm$^{-1}$ * M$^{-1}$) |
| 199 | $6.5 \times 10^4$ |

TABLE 4-continued

UV Maxima for MP470•HCl

| λ-max (nm) | ε (cm$^{-1}$ * M$^{-1}$) |
|---|---|
| 244 | $2.8 \times 10^4$ |
| 291 | $1.8 \times 10^4$ |
| 320 | $2.2 \times 10^4$ |

Figure 2:
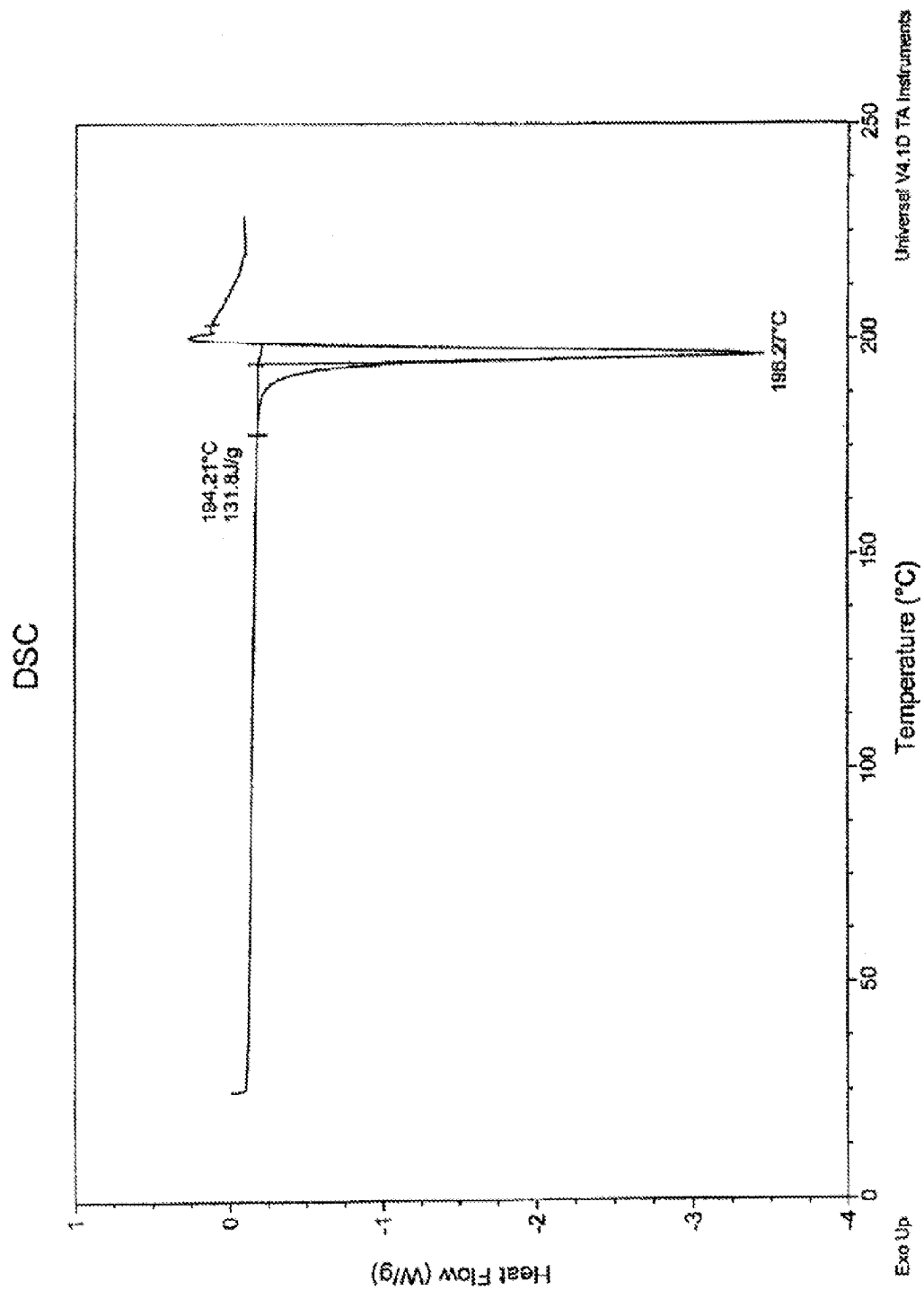
FIG. 2 illustrates a DSC plot of one form of MP470 hydrochloride.

The X-Ray Powder Diffraction (XRPD) pattern of one form of MP470.HCl crystallized from ethanol and hydrochloric acid shows well-defined peaks with high intensities (FIG. 1) suggesting a highly crystalline anhydrate. Differential Scanning Calorimetry (DSC) on the same form shows minor thermal events until 92 and 105° C. A major endotherm is observed at 193° C., which indicates melting of the crystals (FIG. 2).

Figure 3:
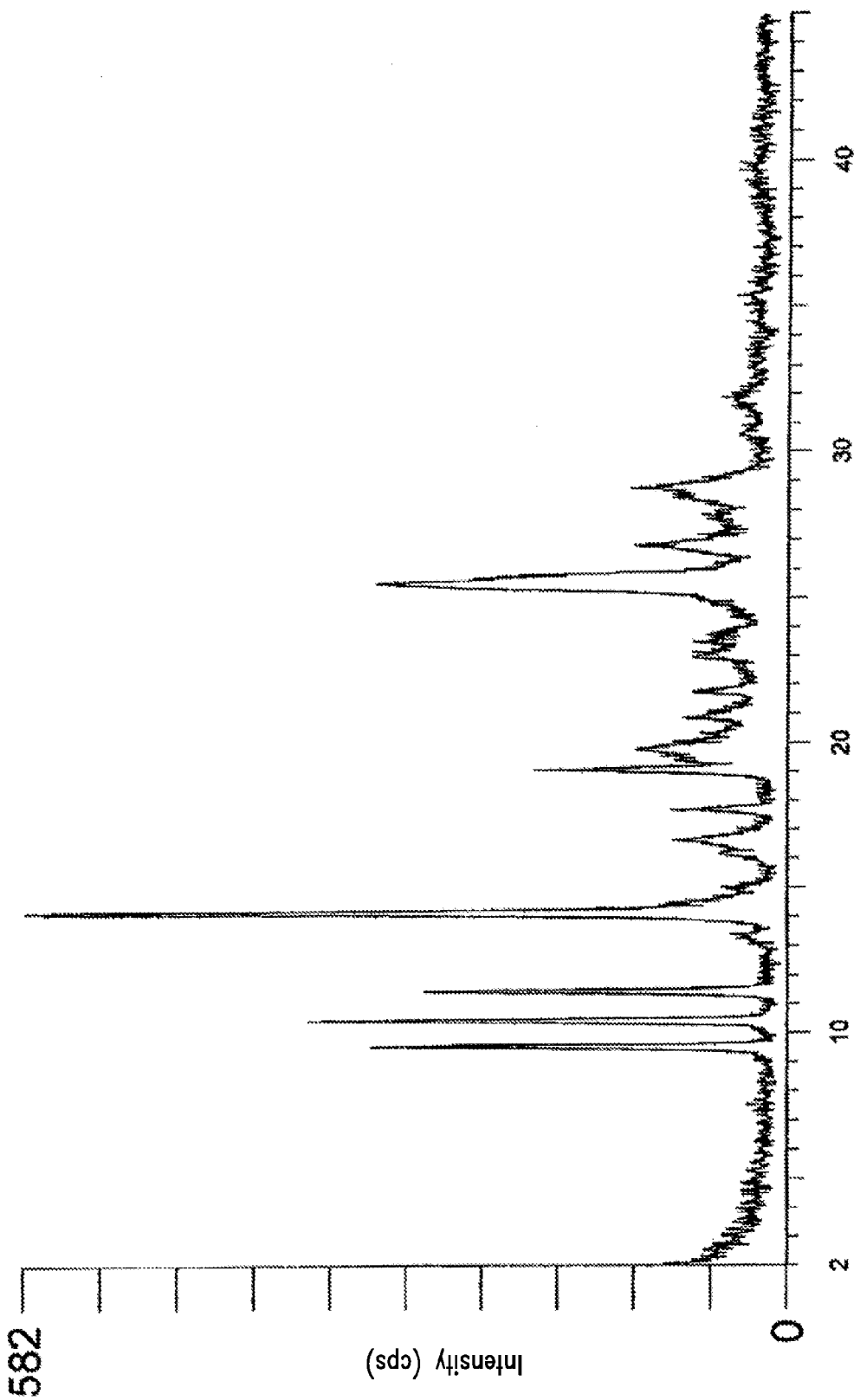
FIG. 3 illustrates a XRD pattern of another form of MP470 hydrochloride.

The X-Ray Powder Diffraction (XRPD) pattern of another form of MP470.HCl shows well-defined peaks with high intensities (FIG. 3) also suggesting a highly crystalline anhydrate.

Single crystal X-ray crystallography confirms the structure, where protonation to form the hydrochloride salt occurs at N1 as shown below.

PDGFRα kinases. The results in Table 5 show that MP470.HCl has potent low nanomolar activity against most of the kinases screened.

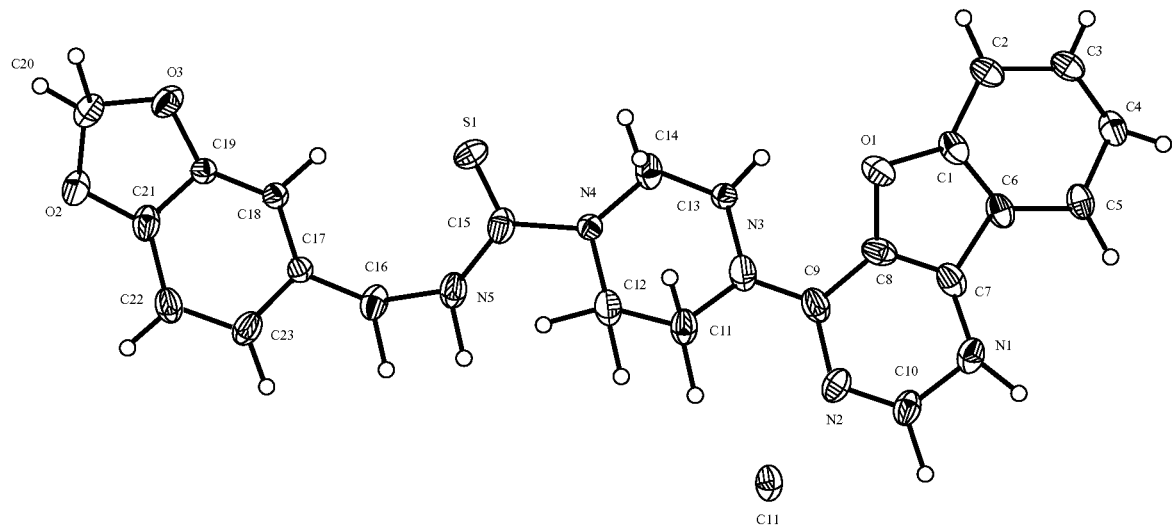

Biological Activity of the Salts Described Herein

IC50 values for MP470.HCl were determined for four mutant c-Kit kinases, one mutant Flt3 kinase, and two mutant PDGFRα kinases.

TABLE 5

IC$_{50}$ values of MP470•HCl against Mutant Kinases

| | IC$_{50}$ values (μM) | | | | | | |
|---|---|---|---|---|---|---|---|
| | cKit (D816V) (h) | cKit (D816H) (h) | cKit (V560G) (h) | cKit (V654A) (h) | Flt3 (D835Y) (h) | PDGFRα (D842V) (h) | PDGFRα (V561D) (h) |
| MP470•HCl | 0.950 | 0.010 | 0.034 | 0.127 | 8.047 | 0.081 | 0.040 |

Figure 4:
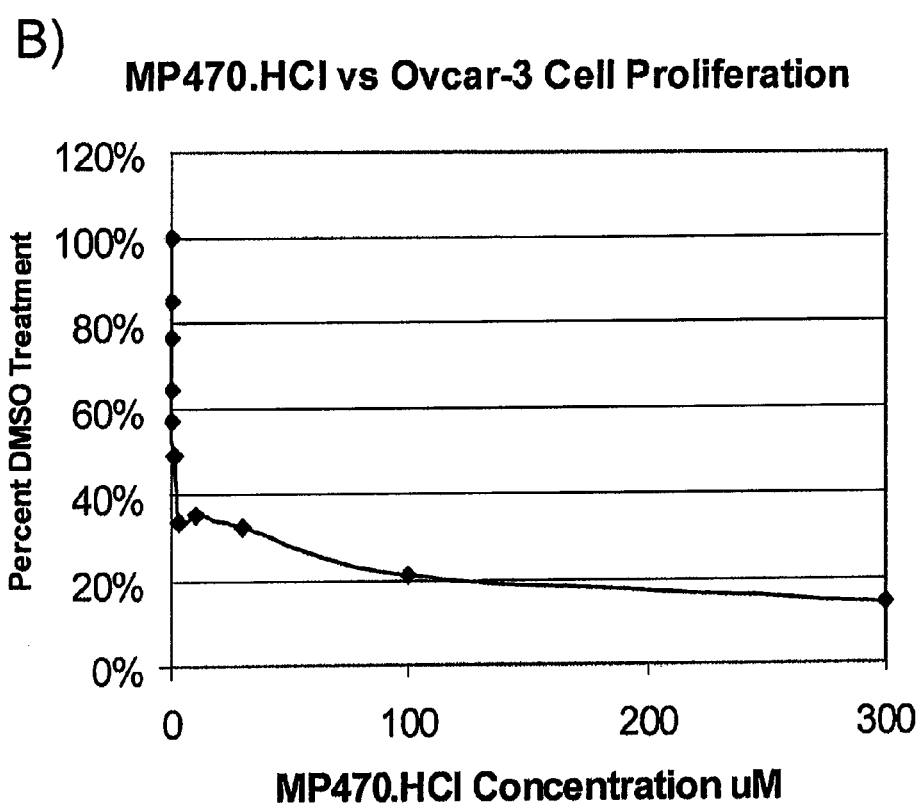
FIG. 4 illustrates the activity of the hydrochloride salt of MP470 on ovarian cancer cells

The IC50 for MP470.HCl on OVCAR-3 cells proliferation was 0.9 µM (FIG. 4). It appears to have a cytostatic effect on cancer cells in addition to being cytotoxic.

Figure 5:
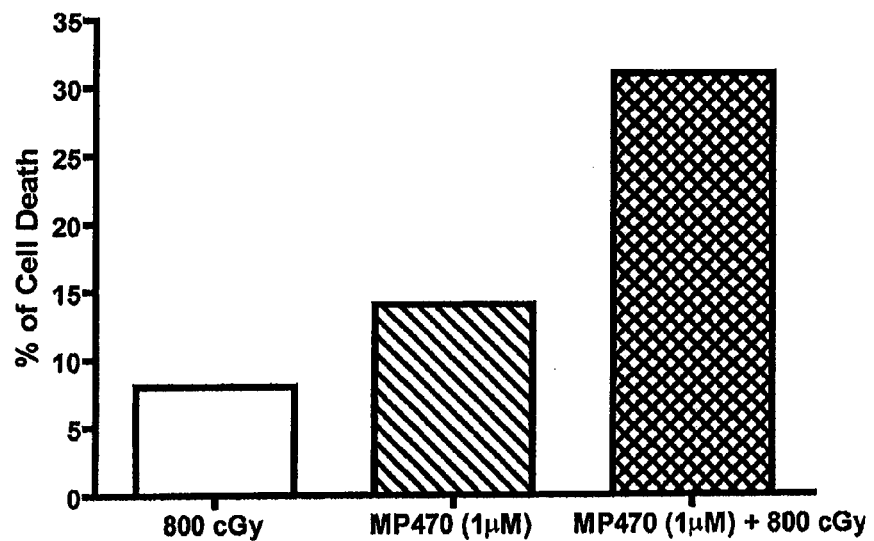
FIG. 5 illustrates the effect of MP470, Ionizing Radiation, and the Combination on Glioblastoma Multiforme Cells

SF-767 glioblastoma multiforme cells were treated with MP470 at 1 µM, 800c Gy IR (ionizing radiation), or a combination of both. Cell death was measured using an MTS (3-(4,5-dimethylthiazol-2-yl)-5-(3-carboxymethoxyphenyl)-2-(4-sulfophynyl)-2H-tetrazolium) assay demonstrating that either MP470 or IR alone will induce cell death, while the combination results in a synergistic effect, increasing cell death by more than two-fold over either agent alone (FIG. 5).

Figure 6:
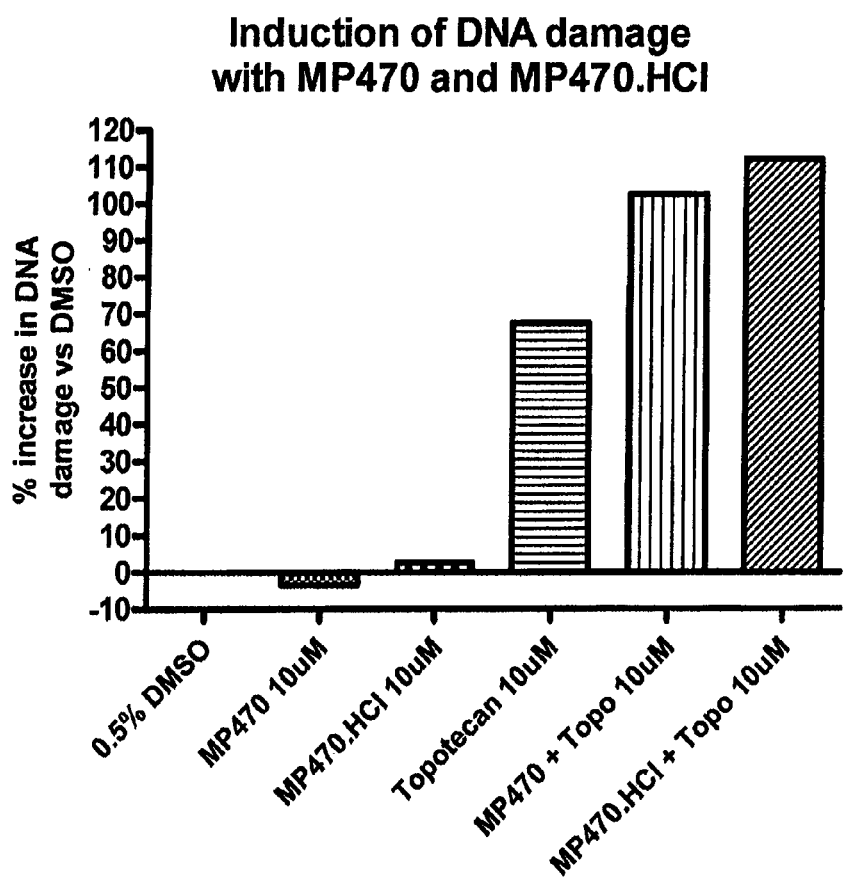
FIG. 6 illustrates the increase in DNA Damage in OVCAR-3 Cells by MP470, MP470.HCl, and Topotecan Alone and In Combination

OVCAR-3 (ovarian carcinoma) cells were treated with MP470 (10 µM), MP470.HCl (10 µM), and/or topotecan (10 µM). Treatment with either MP470 or MP470.HCl alone did not cause DNA damage in these cells as measured by elevation of γ-H2AX levels, while treatment with topotecan increased DNA damage 65% over that of the control (0.5% DMSO medium). In combination, MP470 or MP470.HCl with topotecan increased DNA damage by 103% and 113%, respectively, over that of the control, demonstrating synergy (FIG. 6).

Combination Treatment with MP470.HCl and Platinum-Based Chemotherapy in Non-Small Cell Lung Cancer As with radiation treatment, the sensitivity of cancer cells to platinum-based drugs and other agents which act by damaging DNA may also be mediated by the Rad51 protein. Carboplatin is used frequently for the treatment of non-small cell lung cancer (NSCLC) and in this tumor type positive correlations have been made between high levels of Rad51 and resistance to carboplatin treatment. Therefore, additional experiments were performed in NSCLC cells in order to evaluate Rad51 protein levels and cell sensitivity to carboplatin. If MP470 acts to prevent or inhibit an increase in Rad51 protein levels in response to carboplatin-induced DNA damage, it would be expected that there would be an increase in the sensitivity of cancer cell lines to carboplatin.

The non-small cell lung cancer cell lines A549 and NCI-H647 were used for these experiments. NCI-H647 cells express higher levels of Rad51 compared with A549 cells and have previously been observed to be more resistant to platinum based drugs. The IC50 concentrations observed for carboplatin against both of these cell lines was consistent with this. A549 cells had an IC50 of 20.14 µM and NCI-H647 had an IC50 of 172.53 µM. The IC50 for the HCl salt of MP470 (MP470.HCl) in A549 cells was 6.90 µM, while the NCI-H647 cells IC50 was 7.86 µM.

Two sub-IC50 doses of MP470.HCl were tested in combination with carboplatin to evaluate possible synergism between these agents and consequently a lower IC50 value for carboplatin in each of the cell lines. Doses of 0.71 µM and 3.82 µM MP470.HCl in combination with carboplatin lowered the carboplatin IC50 in A549 cells from 20.14 µM to 6.30 µM and <0.30 µM, respectively. In NCI-H647 cells doses of 0.79 µM and 2.0 µM MP470.HCl lowered the carboplatin IC50 from 172.53 µM to 66.30 µM and 27.03 µM, respectively.

Table 6 below shows IC50 values determined for MP470.HCl, Carboplatin, and combinations of the agents in two NSCLC cell lines. MP470.HCl was able to dramatically decrease the IC50 of carboplatin in these cells.

TABLE 6

Sensitization of NSCLC cells to carboplatin after treatment with MP470•HCl

| A549 NSCLC Cells | MP470•HCl | Carboplatin | Carboplatin + 0.71 µM MP470•HCl | Carboplatin + 3.82 µM MP470•HCl |
|---|---|---|---|---|
| IC50 (µM) | 6.90 | 20.14 | 6.30 | <0.30 |

| NCI-H647 NSCLC Cells | MP470•HCl | Carboplatin | Carboplatin + 0.79 µM MP470•HCl | Carboplatin + 2.0 µM MP470•HCl |
|---|---|---|---|---|
| IC50 (µM) | 7.86 | 172.53 | 66.30 | 27.03 |

Combination Treatment with MP470 and Etoposide in Small Cell Lung Cancer Cells

As with NSCLC, some small cell lung cancer (SCLC) cells also appear to involve Rad51 as a means to develop resistance mechanism to treatment with the DNA damaging agent, etoposide (VP16). Therefore, to determine if MP470 would increase sensitivity to etoposide treatment, SCLC cells were treated with the agents individually and in combination. Using doses below the IC50 for MP470.HCl, we observed a several-fold decrease in the etoposide IC50 compared with that for etoposide alone. The IC50 for MP470.HCl in DMS-153 cells was 5.14 µM, while IC50 in DMS-114 cells was 0.98 µM. Two sub-IC50 doses of MP470.HCl were tested in combination with etoposide to evaluate possible synergism and a resulting lower IC50 value for etoposide in each of the cell lines. Doses of 0.044 µM and 0.62 µM MP470.HCl in combination with etoposide lowered the etoposide IC50 in DMS-153 cells from 0.29 µM to 0.24 µM and 0.026 µM, respectively. In DMS-114 cells doses of 0.10 µM and 0.25 µM MP470.HCl altered the etoposide IC50 from 0.92 µM to 1.98 µM and 0.23 µM, respectively.

Table 7 below shows IC50 determined for MP470.HCl, etoposide, and combinations of these agents in the different SCLC Cell Lines. Thus, at concentrations less than the IC50 of MP470.HCl was able to decrease the IC50 of etoposide in SCLC cells.

TABLE 7

Sensitization of SCLC cells to etoposide after treatment with MP470•HCl

| DMS-153 SCLC Cells | MP470•HCl | Etoposide | Etoposide + 0.044 µM MP470•HCl | Etoposide + 0.62 µM MP470•HCl |
|---|---|---|---|---|
| IC50 (µM) | 5.14 | 0.29 | 0.24 | 0.026 |

| DMS-114 SCLC Cells | MP470•HCl | Etoposide | Etoposide + 0.1 µM MP470•HCl | Etoposide + 0.25 µM MP470•HCl |
|---|---|---|---|---|
| IC50 (µM) | 0.98 | 0.92 | 1.98 | 0.23 |

Rad51 Modulation after Treatment with MP470.HCl

Activity in Tumor Bearing Animal Models

Figure 8:
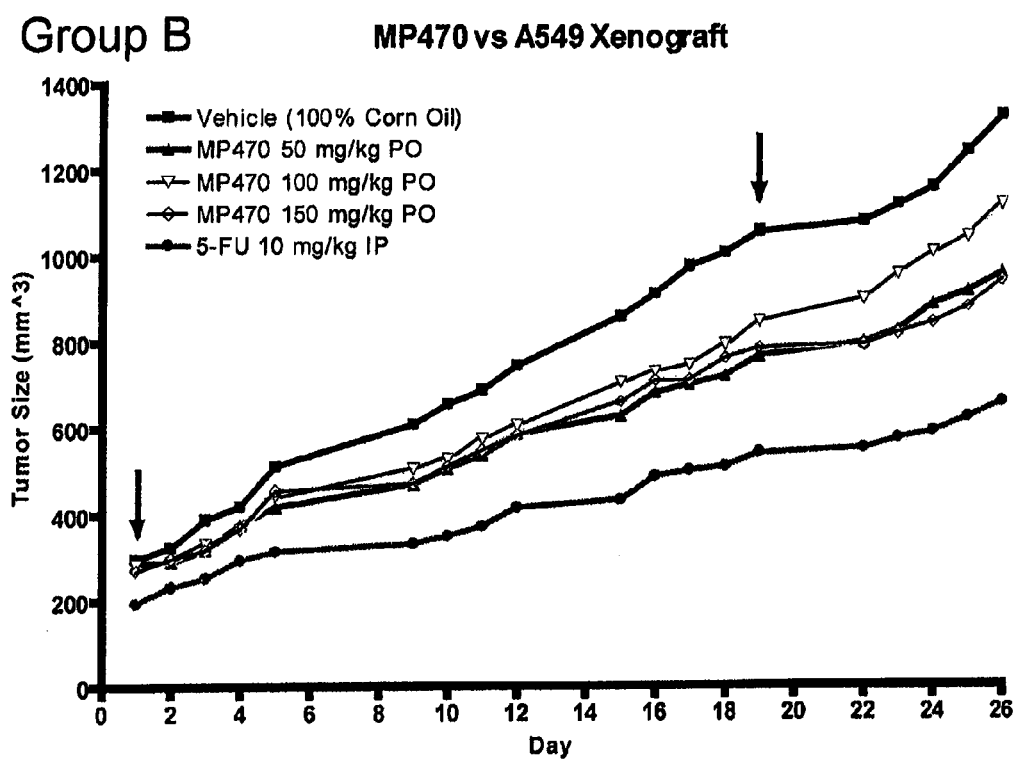
FIG. 8 illustrates the tumor growth reduction in A549 Lung Cancer model by MP470 free base

MP470 and MP470HCl were tested against different tumor types in athymic nude mice as summarized below (Table 8). Various formulations and routes were evaluated. HT-29 colorectal cancer cells and SB-CL2 melanoma cells were implanted subcutaneously, while A549 lung cancer cells, MiaPaCa-2 pancreatic cancer cells, TT medullary thyroid cancer cells, and OVCAR-3 ovarian cancer cells were implanted intradermally in the hind flank of mice. All animals were allowed to develop medium-sized (80-125 mg) tumors, before initiation of dosing. Tumor volume and mouse body-weight were followed over the course of the study.

tained. The results are presented in FIG. 8. MP470 treatment reduced tumor growth rates by Day 26, from 43 mm3/d (vehicle) to rates of 28.3 mm3/d (50 mg/kg), 34.9 mm3/d (100 mg/kg), and 28.1 mm3/d (150 mg/kg). While MP470 reduced

TABLE 8

Activity in In Vivo Murine Tumor-Bearing Models

| Study No. | Drug | Tumor Type | Route | Dose Levels | Schedule | Vehicle* | Outcome |
|---|---|---|---|---|---|---|---|
| 1 | MP470 | HT-29 Colon | IP | 10, 20 mg/kg | (qd × 5) × 2 w | TV-13 | Significant tumor growth retardation No toxicity (weight loss) |
| 2 | MP470 | A549 Lung | PO | 50, 100, 200 mg/kg | (qd × 5) × 2 w | Corn oil | Activity at all three doses without dose dependency No toxicities were noted |
| 3 | MP470 | TT Thyroid | IP | 7.5, 15 mg/kg | (qd×) × 2 w | TV-10 | Dose dependent activity No toxicity |
| 4 | MP470 | SB-CL2 Melanoma | IP | 50 & 75 | qd × 5 | TV-10 | Significant tumor growth retardation Dose dependency |
| 5 | MP470•HCl | MiaPaCa Pancreas | IV | 2.5 mg/kg 5 mg/kg 5 mg/kg | q3d × 28 q3d × 28 q7d × 28 | TV-13 | Frequent dosing had better activity in inhibiting the growth of the tumors |
| 6 | MP470•HCl | OVCAR-3 Ovarian Cancer | PO | 100 or 200 mg/kg | qd × 28 | Corn oil | Significant inhibition of tumor growth Dose dependency Significant combined activity with Cisplatin MP470 (100 mg/kg) + Cisplatin (5 mg/kg) was toxic (mortalities) |
| 7 | MP470•HCl | A459 Lung cancer | PO | 50 mg/kg | qd × 21 | Corn oil | Significant inhibition of tumor growth Dose dependency Significant combined activity with carboplatin MP470 (50 mg/kg) + carboplatin (30 mg/kg) was non-toxic |

Figure 7:
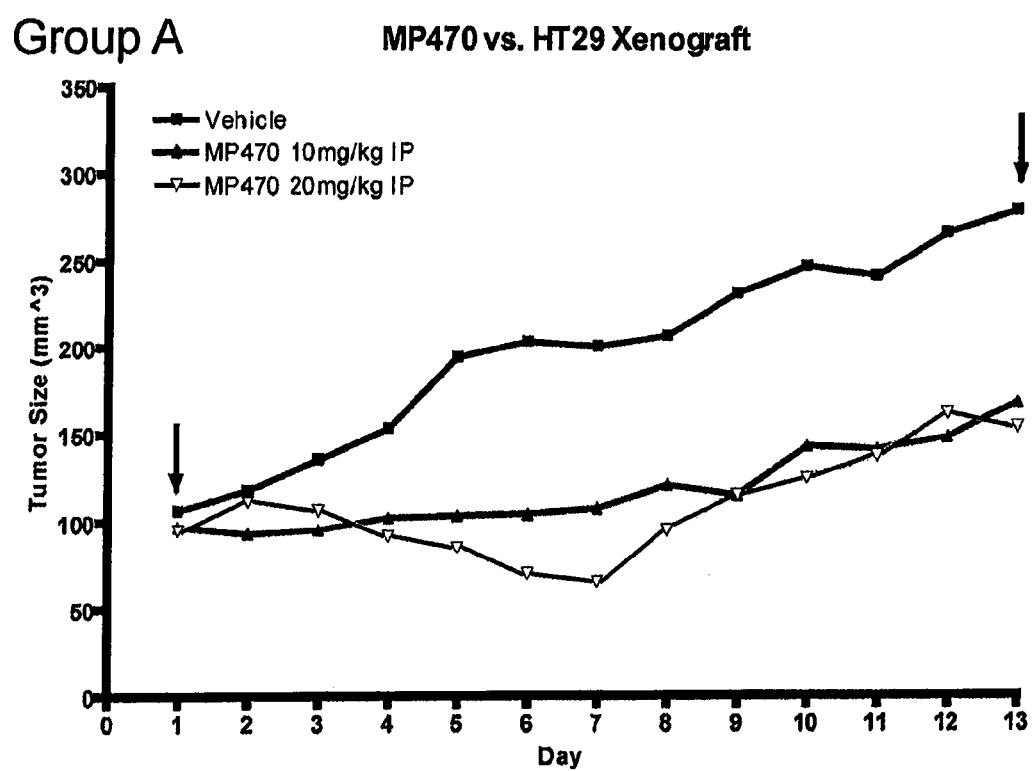
FIG. 7 illustrates the tumor growth reduction in HT-29 colorectal cancer cells by MP470 free base

*TV-10 contains 60% propylene glycol, 30% PEG300, 10% water, and 150 mg/mL 2-hydroxypropyl-β-cyclodextrin; TV-13 contains 5% ethanol, 40% glycerol, 55% water, 300 mg/ml cyclodextrin HT-29 Colorectal Model—Eighteen athymic nude mice were injected subcutaneously with HT-29 colorectal cancer cells. After tumor formation, animals received either 10 or 20 mg/kg MP470 by intraperitoneal (IP) injection using a qd5× 2wk schedule. The results are presented in FIG. 7. On Day 5 of treatment, tumor growth rates in vehicle control animals were 19.5 mm3/d, while MP470-treated animals had tumor growth rates of 1.4 mm3/d (10 mg/kg) and −5.0 mm3/d (20 mg/kg). Tumor growth continued to decline throughout the 14 days of study. On Day 14, the tumor growth rates were 16.4 mm3/d (vehicle) compared to 4.3 mm3/d (10 mg/kg) and 5.5 mm3/d (20 mg/kg) in treated animals. At both doses tested, tumor growth was slowed but not reversed and animals displayed minimal overt toxicity.

A549 Lung Cancer Model—In 40 nude mice implanted intradermally with A549 lung cancer cells, animals were dosed with vehicle orally, MP470 in 100% corn oil orally, or 5-FU in sterile saline IP. MP470 was tested at 50, 100, and 150 mg/kg and 5-fluorouracil (5-FU) was dosed at 10 mg/kg, both with the schedule of qd×5×3wk. Dosing and treatment were well tolerated and the body weights of all mice were maintumor growth rates, treatment of these cells with 5-FU reduced the overall tumor growth rate per day further to 19.5 mm3/d on Day 26. There was no apparent dose relationship in the MP470 effect.

Figure 9:
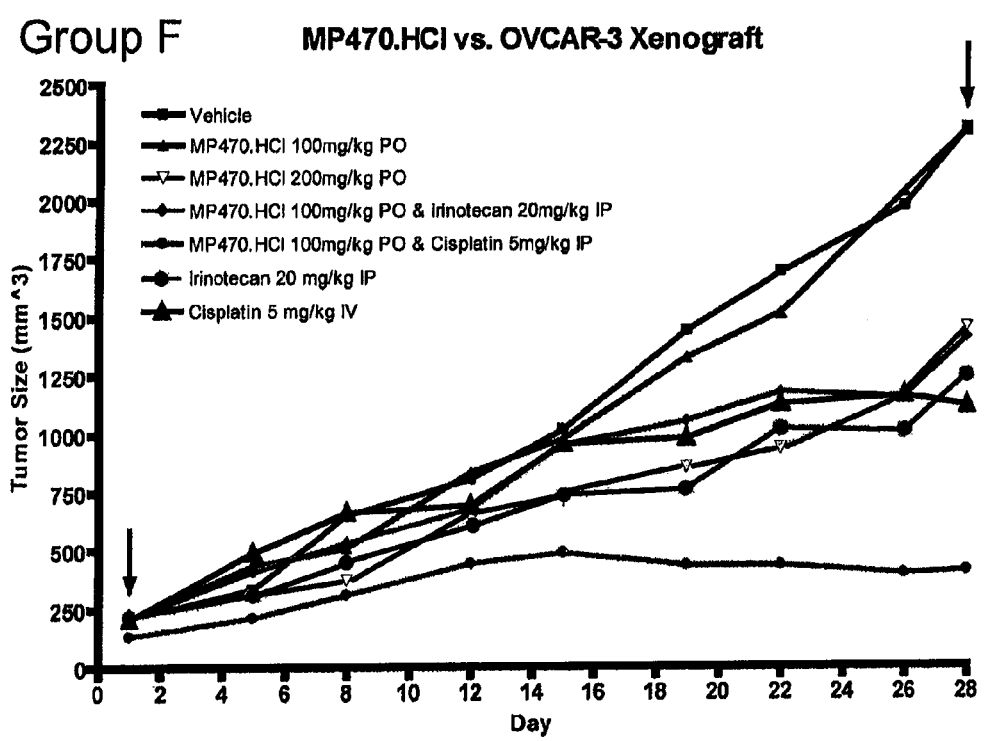
FIG. 9 illustrates the tumor growth reduction in OVCAR-3 Ovarian Cancer Model by MP470 hydrochloride salt

OVCAR-3 Ovarian Cancer Model—Forty-two nude mice were implanted subcutaneously with OVCAR-3 ovarian carcinoma, the hydrochloride salt of MP470 (MP470.HCl) was formulated in 100% corn oil and delivered orally. MP470.HCl, cisplatin, and irinotecan were administered to animals alone or in combination. When administered alone, MP470.HCl was given qd at 100 or 200 mg/kg, irinotecan was given q3d at 20 mg/kg, and cisplatin was given q7d at 5 mg/kg. In combination studies, 100 mg/kg MP470.HCl was given qd and combined with 20 mg/kg irinotecan given q3d or 5 mg/kg cisplatin given q7d. One animal in the 200 mg/kg MP470.HCl group died on Day 1, while five animals in the MP470.HCl/cisplatin combination group died (one on Day 5, Day 6, Day 7, Day, 20, and Day 27). The tumor growth reduction results are presented in FIG. 9. Treatment with each individual agent (200 mg/kg MP470.HCl, 46.2 mm3/d; 20 mg/kg irinotecan, 38.53 mm3/d; 5 mg/kg cisplatin, 33.8 mm3/d) reduced the tumor growth rate below that of vehicle-treated mice (78.04 mm3/d). When animals were treated with the combination of MP470.HCl and irinotecan, the tumor growth rate was 44.6 mm3/d, demonstrating that there is not an additive or synergistic effect with the combination. In contrast, when MP470.HCl and cisplatin were used in combination, the tumor growth rate was reduced to 10.22 mm3/d. However, the 100 mg/kg dose of MP470.HCl in combination with cisplatin caused enhanced toxicity and most animals in this group died during the 21-day treatment period. The enhanced toxicity was related to the level of the dose used, so a subsequent study was conducted using half the dose, 50 mg/kg/day as described below.

Figure 10A:
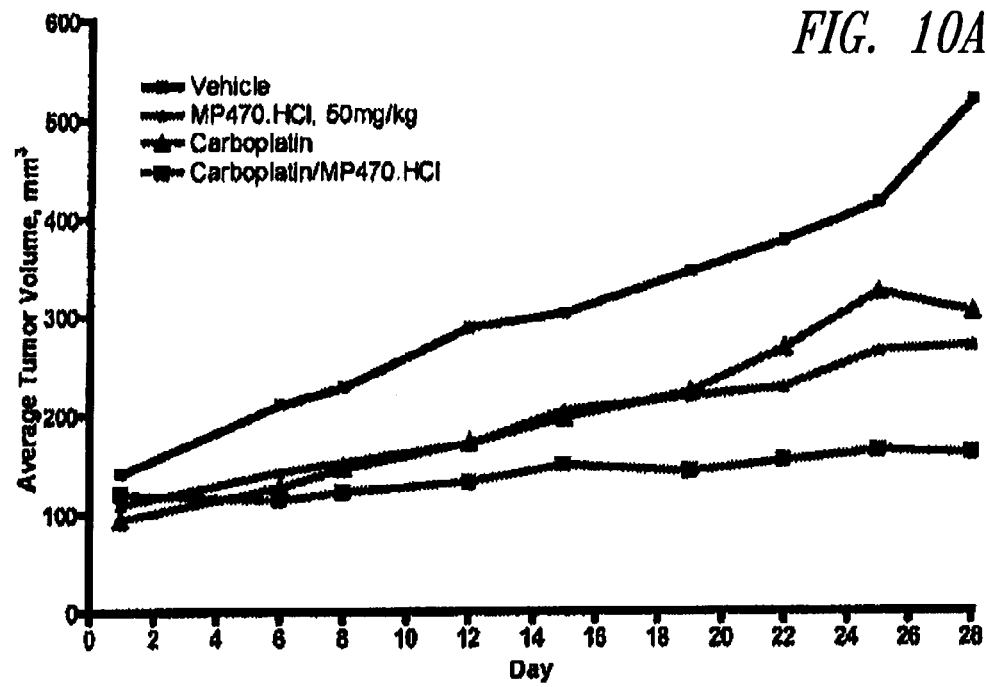
FIGS. 10A and 10B illustrate the tumor growth reduction in A549 Non Small Cell Lung Cancer by MP470 hydrochloride salt
Figure 10B:
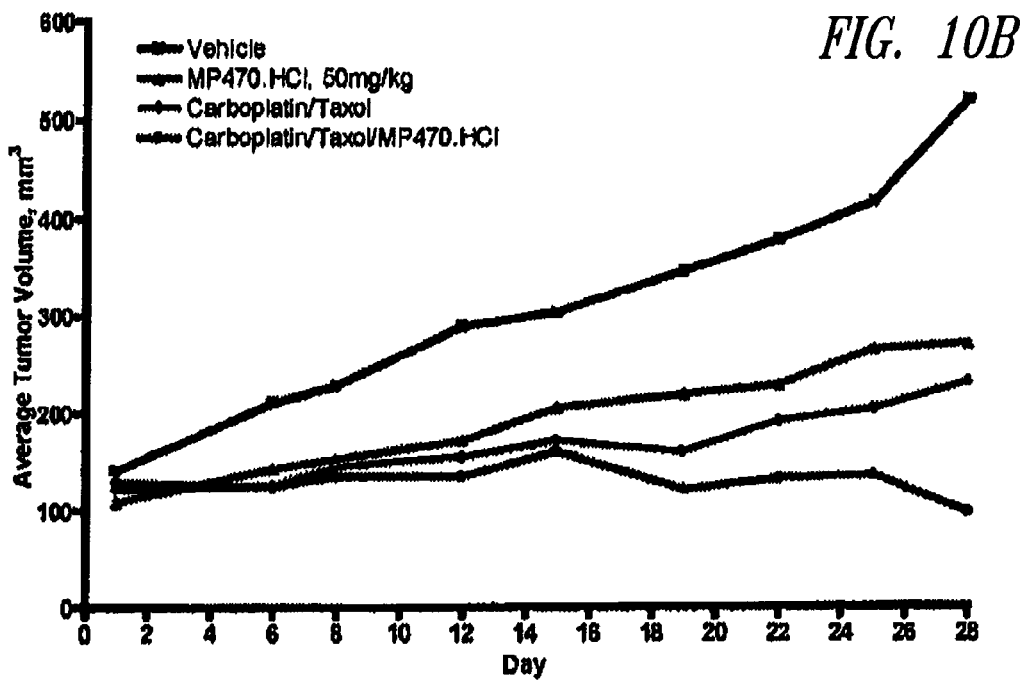

To determine whether MP470.HCl in combination with carboplatin increased the anti-tumor activity in xenograft tumors growing in vivo, the agents were administered alone and in combination and tumor growth was monitored. MP470.HCl (50 mg/kg) was combined with carboplatin (30 mg/kg) alone or carboplatin with taxol (20 mg/kg). When used in combination with carboplatin alone or carboplatin/taxol, a decrease in the tumor growth rates for both combinations were observed when MP470.HCl was included (FIG. 10)

Reduction of Erk Phosphorylation by MP470 Hydrochloride

Figure 11:
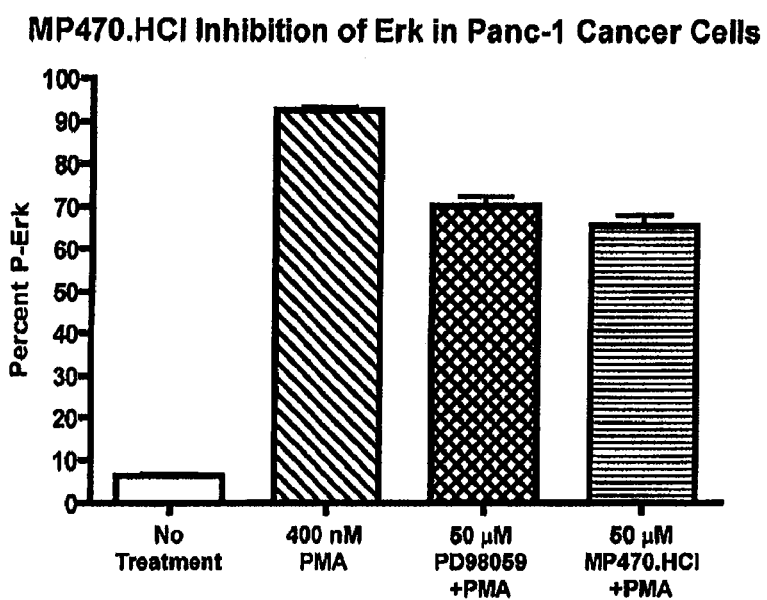
FIG. 11 illustrates the Erk phosphorylation changes in Panc-1 Pancreas Cancer Cells after MP470 hydrochloride exposure
Figure 12:
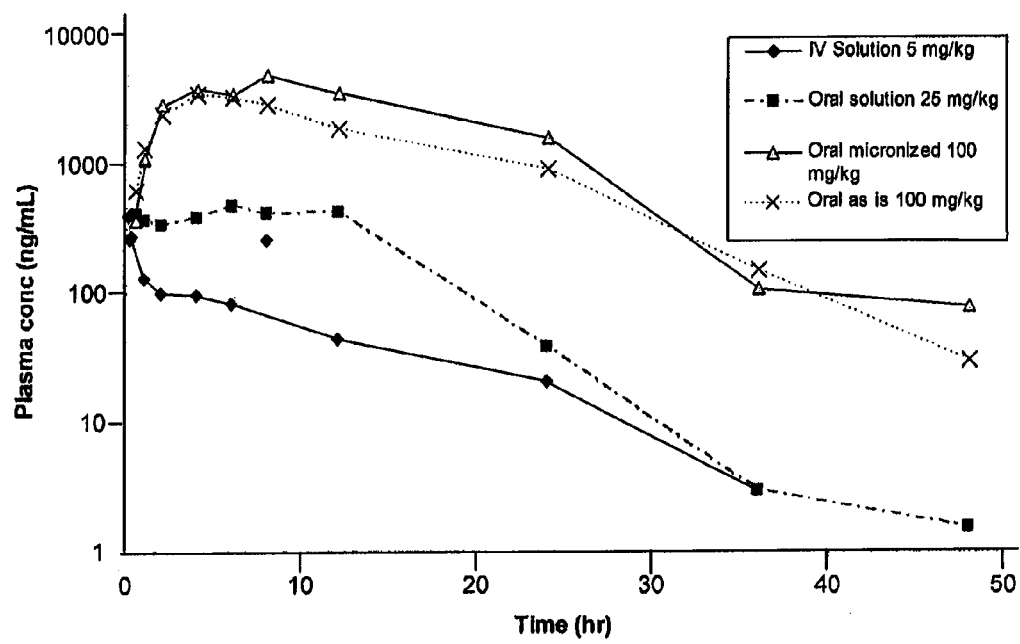
FIG. 12 illustrates the plasma-time (Log) Plot for various dosage forms of MP470 hydrochloride administered either intravenously or orally

Regulation of Erk phosphorolation—MP470.HCl activity was screened against potential biomarkers, including proteins, such as Erk that are activated downstream of c-Kit. Erk was selected from potential candidate markers to evaluate changes in protein phosphorylation in treated cancer cell lines because MP470 appeared to regulate this event. MP470.HCl reduced the level of Erk phosphorylation compared to phorbol myristate acetate (PMA) treatment alone (FIG. 11). Exposure to PMA is known to rapidly stimulate Erk phosphorylation and was used as a positive control. MP470.HCl reduced the level of P-Erk below that of PD98059, an Erk-specific inhibitor, suggesting that MP470.HCl is a more potent inhibitor at this concentration.

Suppression of Rad51 Expression by MP470 Hydrochloride

MP470.HCl sensitizes cancer cells to the effects of treatment with DNA damaging agents due to alteration of Rad51 expression. Rad51 (a eukaryotic homologue of *Escherichia coli* RecA) is similar to RecA, both biochemically and structurally. It promotes homologous pairing and strand exchange within a regular nucleoprotein filament. In mammalian cells, seven genes in this family have been identified (HsRAD51, XRCC2, XRCC3, RAD51B/hREC2 and HsDMC1, RAD51C, and RAD51D). Recent studies suggested that RAD51 is involved not only in homologous recombination but also in cell proliferation regulation.

Rad51 protein levels were also determined in A549 non-small cell lung cancer cells using combinations with DNA damaging agents. Cells were treated for 24 hrs with 6.1 µM (IC30 of carboplatin alone) carboplatin in combination with 0.71 µM or 3.82 µM MP470.HCl. Protein lysates were isolated from treated and non-treated cells, separated by SDS-PAGE, and transferred to nitrocellulose. Probing blots for Rad51 showed that treatment with MP470.HCl alone did not alter the expression of Rad51. Conversely, carboplatin treatment dramatically increased Rad51 levels 12-fold over non-treatment levels. The increase in Rad51 due to carboplatin treatment was reduced by 26% when treated in combination with 0.71 µM MP470.HCl and by 42% with 3.82 µM MP470.HCl To determine if the effects of Rad51 modulating activity could be observed in vivo and would result in improved efficacy in vivo, we dosed HT-29 xenograft tumors with cisplatin or MP470.HCl in combination with cisplatin. Western blotting for Rad51 levels in these treated tumors revealed that Rad51 was 2.11 fold higher in cisplatin treated tumors than in tumors treated in combination with MP470.HCl.

Western blotting for Rad51 in cancer cell lines showed an increase in Rad51 protein when cells were exposed to ionizing radiation (IR) (Daboussi, F., Dumay, A., Delacote, F., Lopez. B. S., "DNA double-strand break repair signaling: the case of RAD51 post-translational regulation," *Cell Signal* 12:969-75 (2002)). Conversely, in cells pretreated with MP470, Rad51 remained near control levels even after exposure to IR. Similar to IR, the sensitivity of cancer cells to platinum-based drugs can be affected by the level of Rad51 protein.

A study was performed to develop a testing procedure for validation of IHC Biomarker RAD51 for the staining of tissue micro arrays (TMA). An experimental non-small cell antibody was used (Spring Bioscience Anti-RAD51) and run using testis and lung as control tissues. The antibody was run using the Dako Envision+ detection kit. The incubation times ranged from 15 minutes to 60 minutes. Each experiment was run with and without an antigen retrieval solution with a pH of 6.0. The dilutions used for the Spring Bioscience Anti-RAD51 ranged from 1:50 to 1:500. The best results were obtained when incubated for 30 minutes, with a dilution of 1:50, using the Dako Envision+ detection kit, with antigen retrieval at the pH of 6.0 based on manual scoring by a board certified pathologist. This dilution exhibited strong nuclear staining in the testes sample that was stained. At this dilution the non-small cell lung samples exhibited mainly cytoplasmic staining in varying degrees of intensity. Rare nuclear staining was observed. The tissue microarray (TMA) stained slide exhibited mainly cytoplasmic staining with occasional nuclear staining.

A study was conducted to investigate the changes in RAD51 expression levels after chronic treatment with MP470 hydrochloride salt two weeks post treatment with oral once daily dosing for 28 days at 300 mg/kg compared to the control (vehicle only, no drug) to healthy dogs. Tissue specimens from the colon and skin were analyzed for RAD51 expression using the procedure described above. The data in Table 9 confirm that MP470.HCl suppresses and sustains the suppression of RAD51 expression levels in normal proliferating tissues such as in colon and skin.

TABLE 9

Rad51 expression changes after chronic treatment with MP470 hydrochloride salt

| Assay | Dose | Dog ID # | Tissue Origin | Result |
|---|---|---|---|---|
| Rad 51 | 2 wk post treatment with 300 mg/kg/day × 28 | 302786 Group 1 | Colon | 58% |
| Rad 51 | 2 wk post treatment with 300 mg/kg/day × 28 | 302786 Group 1 | Skin | 12% |
| Rad 51 | No drug | 302821 Group 4 | Colon | 19% |
| Rad 51 | No drug | 302821 Group 4 | Skin | 7% |

Bioavailability of the Salts Described Herein

MP470 (free base) given orally as a single dose of 100 mg/kg in a dry powder blend to four rats per group resulted in an AUC of 7.9 μg.h/mL versus 100 mg/kg of MP470.HCl in a similar blend generated an AUC of about 94 μg.h/mL (Table 10). MP470 free base has a relative bioavailability of ~8% as compared to the HCl salt. The Cmax for MP470.HCl given 100 mg/kg orally ranges from 4.6-7.2 μg/mL and the Tmax from 4.0-9.5 h.

higher at 100 mg/kg than at 25 mg/kg and the increases in AUC0-∞ were greater than dose-proportional. For a 4-fold increase in dose level, the average AUC0-∞ value increased 13.1-fold for males and 9.9 fold for females suggesting saturable clearance.

TABLE 10

Table Pharmacokinetic Parameters in Rat

| Species | Dose; Route of Administration | Drug | Vehicle | $t_{1/2\beta}$ (h) | $T_{max}$ (h) | $C_{max}$ (μg/mL) | $AUC_{0 \to last}$ (μg · h/mL) |
|---|---|---|---|---|---|---|---|
| Rat | 100 mg/kg; PO | MP470•HCl | Dry Blend** | — | 9.5 | 7.19 | 94.31 |
| | 100 mg/kg; PO | MP 470 | Dry Blend** | — | 11.3 | 0.71 | 7.91 |
| | 100 mg/kg; PO | MP470•HCl | Corn oil | — | 4.0 | 5.27 | 73.35 |
| | 3 mg/kg; IV bolus | MP470•HCl | TV-10*** | 0.36 | 0.02 | 8.53 | 18.81 |

**Dry Blend comprises sodium lauryl sulfate (SLS) at 50% of drug + calcium carbonate
***TV-10 comprises 60% propylene glycol, 30% PEG300, 10% water, and 150 mg/mL 2-hydroxypropyl-β-cyclodextrin Twenty-four rats were placed into four groups each consisting of three animals per sex. The animals were weighed the day before dosing, as well as just prior to dosing. The test articles were administered once as presented in Table 11. The plasma concentration-time plots are presented in FIG. 13.

After oral administration of micronized MP470.HCl (Group 4), peak plasma concentrations of MP470 were attained at 4-12 hours. The extent of systemic exposure of rats to MP470, characterized by AUC0-∞, was approximately 3.4-fold higher in females than in males for Group 4. The

TABLE 11

Pharmacokinetic study design for rats treated by different routes and forms of MP470•HCl

| Group | No. of Animals (M/F) | Test Articles | Route of Exposure | Dose Level (mg/kg) | Dose Conc. (mg/mL) | Dose Volume (mL/kg) |
|---|---|---|---|---|---|---|
| 1 | 3/3 | Non-micronized MP470•HCl[a] | Intravenous Infusion (30 min) | 5 | 1.25 | 4 |
| 2 | 3/3 | Non-micronized MP470•HCl[a] | Oral Gavage | 25 | 1.25 | 20 |
| 3 | 3/3 | Non-micronized MP470•HCl[b] | Oral Gavage | 100 | 20 | 5 |
| 4 | 3/3 | Micronized MP470•HCl[b] | Oral Gavage | 100 | 20 | 5 |

[a]Dosed as a suspension in a 20% w/v aqueous solution of Captisol ®
[b]Dosed as a suspension in a 0.5% w/v aqueous suspension of sodium carboxymethyl-cellulose After intravenous infusion of MP470.HCl at 5 mg/kg, average MP470 peak plasma concentrations of 454.3 ng/mL for males and 370.7 ng/mL for females were attained at 0.083 hours (5 minutes), the first sampling point postdose. After oral administration of non-micronized MP470.HCl, peak plasma concentrations of MP470 were attained at 0.5-12 hours for Group 2 (25 mg/kg) and 4-12 hours for Group 3 (100 mg/kg, suspension). The extent of systemic exposure of rats to MP470, characterized by AUC0-∞, was approximately 3.8-fold and 2.9-fold higher in females than in males for Groups 2 and 3, respectively. Average AUC0-∞ values were extent of exposure of rats to MP470, characterized by AUC0-∞, was 1.7-fold (males) and 1.4-fold (females) higher for non-micronized MP470HCl (Group 3) than for micronized MP470HCl (Group 4).

The oral bioavailability of non-micronized MP470HCl is summarized in Table 12 and was estimated to be 43.40% for males and 100.21% for females.

TABLE 12

| Bioavailability of MP470•HCl in Rats | | | | | | | |
|---|---|---|---|---|---|---|---|
| Test Article | Group Number | Route | Dose Level (mg/kg) | Gender | $t_{1/2\,(h)}$ | AUC INF (hr * ng/mL) | Bio-availability (%) |
| MP470•HCl Solution | 1 (3M/3F) | IV | 5 | Female | 2.6-2.9 | 2530.9 | — |
| | | IV | 5 | Male | 3.1-4.4 | 1546.3 | — |
| | 2 (3M/3F) | Oral | 25 | Female | 4.0-17.4 | 12681.6 | 100.21% |
| | | Oral | 25 | Male | 2.8-4.2 | 3355.1 | 43.40% |

Tolerability of the Salts Described Herein

Acute Toxicity of MP470 Free Base Delivered Intravenously

The purpose of these studies was to determine the highest level of MP470 free base that can be administered intravenously to dogs without causing extreme illness, maximum tolerated dose (MTD). In both studies a single male and a single female beagle dog were injected intravenously with MP470. Animals were observed for signs of toxicity, immediately and one-hour post-dosing, and daily on non-dosing days.

In the first study, 2 doses of MP470 were tested, a low dose of 10 mg/kg followed 48 hours later by a dose of 20 mg/kg. Dosage escalation stopped after the 20 mg/kg dose due to observations of adverse clinical signs. After the second dose, the animals were observed everyday for 3 additional days for adverse clinical signs. Over the course of the 5 days of study both dogs gained weight. After the administration of the 10 mg/kg dose no adverse clinical signs were observed in the male dog. The female dog experienced retching immediately after dosing. Upon administration of the 20 mg/kg dose both the female and male dog experienced unacceptable adverse effects. After three more days of observation both dogs were euthanized and necropsy was performed. The necropsy observations considered abnormal include thrombus observed in the dosing veins of both dogs and possible mild venous congestion in the meningeal vein between brain hemispheres and in the venous sinus on cranial floor of the male animal. From this study the maximally tolerated dose in beagle dogs was determined to be 20 mg/kg.

In the second study we tested doses of 0.625, 1.25, 2.5, 5, 10, and 20 mg/kg MP470 in 1 male and 1 female beagle dog with 48-96 hrs between dose escalations, with the exception of 11 days between dose 5 and 6. Additionally, in this study approximately 5-10 second electrocardiograph (ECG) tracings in a lead ii configuration were obtained from each dog prior to each dose, approximately 20 minutes after the start of dosing, and immediately after completion of dosing. Both animals appeared normal at all times prior to, during, and after doses 1 through 5 and prior to dose 6. During dose 6 administration, vomiting, anxiety, facial swelling, urination, defecation, depression, and recumbency were noted. The female dog died within 5 minutes of the completion of dose 6 administration and the male dog appeared normal by the following day after the dose 6 administration. The animals appeared normal on all non-dosing days. Both dogs gained weight over the course of the study (21 study days). Test article related necropsy observations included: intestinal mucosal congestion and meningeal vessel congestion for the female and lung congestion for the male. Under the conditions of this study, the acute maximum tolerated dose of MP470 administered as an intravenous infusion over 30 minutes in the Beagle dog is considered to be 10 mg/kg based on criteria of abnormal clinical observations, ECG tracings, and gross necropsy observations. Because no concentration of MP470 were tested between 10 mg/kg, where there was acceptable side effects, and 20 mg/kg, where there was unacceptable side effects, we can not recommend from these data an acute MTD above 10 mg/kg.

In the first IV administration study of MP470 free base, six groups of 6 rats were to be exposed to either vehicle alone or MP470 at 10, 20, 40, 80, or 160 mg/kg. Dosing was administered via a tail vein over approximately 30 minutes. Animals were observed immediately and 10 minutes and one hour after dosing, and daily thereafter for 4 additional days. All six control animals received the vehicle and were observed with red urine, lethargy, and ataxia immediately and up to 1 hour after dosing, but recovered and appeared normal thereafter. Only three animals were administered the low dose of MP470 because the third rat died after dosing, therefore further dosing ceased. The two surviving animals were observed to have red urine, recumbency, and labored breathing immediately and 10 minutes after dosing. Red urine and lethargy were present at 1 hour post dosing, but animals recovered and appeared normal thereafter. The animal that died after dosing was necropsied and displayed red tinged urine and dark red mottled lungs. All other animals were euthanized and necropsied at day 4 appeared normal.

In the second IV administration study of MP470 free base, six groups of 6 rats were to be exposed to either vehicle alone or MP470 at 0.625, 1.25, 2.5, 5, or 10 mg/kg. Dosing was administered via a tail vein over approximately 30 minutes. Animals in each group were given a single intravenous dose of the test substance. Animals in the lowest dose group were dosed first, followed by at least a 10 minute period to observe any effects. If no effects were observed or if effects were observed but deemed acceptable the dosing went to the next highest dose using the same progression criteria. Progression was stopped when unacceptable, adverse effects (e.g., severe convulsions or death) occurred or when the highest dose was successfully administered without adverse effects. A control group (formulation vehicle: TV-13) was included for relevant comparison. The animals were observed for signs of toxicity, immediately, 10 minutes, and one hour post-dosing, and daily thereafter for 4 days. Dosing occurred on Day 0 and termination on Day 4. On Day 4, the animals were sacrificed and subjected to complete, documented, gross necropsy.

Mortality (50%) occurred in the high dose group (10 mg/kg). Some of the animals in the vehicle control and some of the animals in all test article groups were observed with red urine and/or wobbly and ataxic appearance immediately, 10 minutes, and 1 hour after dosing. In general, there was a decrease in body weight for all groups on Day 2 and the majority of the vehicle control animals still had a lower body weight on day 4. With the exception of the high dose group, there appeared to be a correlation for the incidence of adverse findings with the volume of vehicle administered (i.e., higher incidence with higher volume). At necropsy on Day 4, all surviving animals appeared normal, whereas, the high dose animals that died on Day 0 had correlative adverse findings of dark red congestion at the base of the heart and/or red urine in the bladder and bright red lungs. Under the conditions of this study, a maximum tolerated acute dose in the rat for MP470 was determined to be 5 mg/kg. However, a 'no observable adverse effect level' could not be determined due to adverse observations apparently associated with vehicle administration.

Acute Toxicity of MP470 Hydrochloride Salt Delivered Orally

Four groups of Sprague Dawley rats, each consisting of two males and two females, received escalating single doses of 100, 200, 800 and 2000 mg/kg of the test article. MP470.HCl was suspended in an aqueous vehicle constituting 0.5% w/v carboxymethylcellulose and administered by oral gavage. The animals were observed at 1, 2.5, 4, and 24 hr post dosing. Additionally, the dose group of 2000 mg/kg was observed at 48 and 72 hr post dosing. Doses were based on body weights on the day of dosing. The animals were euthanized after the last observation. All doses were well tolerated by both genders assessed based on absence of clinical abnormalities and gross necropsy lesions. A single oral dose no-observed-effect level (NOEL) was 2000 mg/kg. Acute maximum tolerated dose (MTD) was greater than 2000 mg/kg (highest dose tested).

Two groups of dogs, each consisting of one male and one female, received alternating escalating single doses of 30, 60, 240, 1000, and 2000 mg/kg of the test article. MP470.HCl was administered by capsule. Animals were observed for clinical abnormalities over a 24 hr period and toxicokinetics was conducted on animals administered with 1000 and 2000 mg/kg test article. All doses were well tolerated by both genders. No test article related mortalities or clinical signs of toxicity were observed. Test article related effects were limited to emesis following administration of 1000 and 2000 mg/kg doses. Single oral dose NOEL was determined to be 240 mg/kg and the acute oral MTD was 2000 mg/kg (highest dose tested).

Chronic Toxicity of MP470 Hydrochloride Salt Delivered Orally

In a chronic tolerability study of MP470 hydrochloride salt in the rat, the animals were dosed 20, 60, 100 or 200 mg/kg/d (males) and 6, 20, 60 and 100 mg/kg/d (females) daily for 28 days. One female rat died after 5 doses at 100 mg/kg/d, however the it was not clear if this was related to the drug. Two additional female rats died on days 28 and 42 (control and 60 mg/kg/d) possibly due the trauma induced by repeated blood collection. There were no clinical signs of severe toxicity prior to deaths. The clinical abnormalities included hunched posture, soft feces and sporadic occurrence of hair loss. There was no clear dose dependency. Although all animals gained weight during the study, the relative gain was lower in the males at 200 mg/kg/d (70% control) and females at 60 and 100 mg/kg/d (83 and 57% control). Animals in these groups also exhibited a corresponding decrease in food consumption. There were signs of recovery after cessation of dosing. There were no drug related adverse opthalmologic effects or change hematology parameters. Significant clinical chemistry changes included decreases in glucose and triglyceride levels in males at 200 mg/kg/d, and alterations in cholesterol, troponin-1 and alkaline phosphatase in females (60 and 100 mg/kg/d). There was no correlative histopathology for these alterations. There were no drug related adverse changes in urinalysis or organ weight changes. There were sporadic alterations in organ weights but without corresponding microscopic pathology. Histopathology revealed no adverse effects in any organ and there was no evidence of cardiotoxicity in either sex. There was adequate systemic exposure in both sexes; however the exposure was not dose-proportional (lower at higher doses). At all doses exposure to females was higher than that in males and exposure on day 27 was higher than that on day 1. There was substantial variability in the half-lives and ranged from 2 to 8 hours. The no observed effect level (NOEL) was 60 mg/kg/d (360 mg/m2/d) for males and 20 mg/kg/d (120 mg/m2/d) for females. In the absence of clear target organ toxicity or signs of severe toxicity a severely toxic dose (STD) could not be calculated. STD is likely to be higher than 100 mg/kg/d for females and 200 mg/kg/d for the males.

In a chronic tolerability study of MP470 hydrochloride salt in the dog, groups of six male and six female dogs received 0, 30, 100, or 300 mg/kg/day of the test article (Groups 1-4, respectively) for 28 days. MP470.HCl was administered, by capsule, as a dry powder blend with sodium lauryl sulfate. There were no mortalities. In males, increased incidences of emesis and soft feces/diarrhea for Groups 3-4 and discolored and mucoid feces for Groups 2-4 were observed. In females, increased incidences of emesis and mucoid feces for Group 4, increased incidences of soft feces/diarrhea for Groups 3-4, and discolored feces for Groups 2-4 were noted. These clinical abnormalities were not considered adverse. No test article-related effects on body weight or food consumption were observed during the dosing or recovery periods. No test-article related lesions were noted during ophthalmic examinations and all electrocardiograms of the test and control animals were within normal limits. No test article related effects on hematology or urinalysis parameters were observed during the dosing or recovery periods.

Test article related effects on clinical chemistry parameters during the dosing period were limited to lower mean serum aspartate aminotransferase (75%) and plasma thyroxine (50%) levels for the Group 4 males when compared with the control group. No test article related changes in serum troponin 1 levels were observed in either sex for the dosing-period animals. Test article related organ weight changes during the dosing period were limited to higher mean liver weights (124, 123 and 119%, respectively) and mean liver weights relative to brain weights (117, 121 and 120%, respectively) for the Group 2-4 females when compared with the control group. Test article related organ weight changes during the recovery period were limited to statistically lower mean heart weights relative to body weight for the Group 3-4 females (85 and 89%, respectively) when compared with the control group. No test article-related gross or microscopic lesions were observed for the dosing or recovery period animals. There were no histopathological alterations in the cardiac tissues suggestive of cardiac injury in either sex.

There was adequate systemic exposure, in general plasma concentration of the test article increased relatively rapidly after treatment, followed by a steady decline for all dose groups and both sexes. Systemic exposure to the test article, as measured by Cmax and AUC, increased with increasing dose in both sexes, but the increase was generally less than dose proportional. No significant differences in exposure to the test article were observed between male and female dogs. No accumulation of the drug was evident as measured by difference in exposure between day 0 and day 27. The time to reach maximal plasma concentration (t-max) ranged from 2-4 hours for Groups 2 and 3 and ranged from 2-8 hours for Group 4. The terminal half-lives varied widely and ranged from 7-84.7 hours for Group 2, 16-47.7 hours for Group 3 and 10.5-28 hours for Group 4. The Cmax ranged from 42.5-153.6 ng/mL for Group 2, 78.3-231 ng/mL for Group 3 and 192.4-329.2 ng/mL for Group 4. There was a large variability in exposure. The AUC all ranged from 97.9-1128.3 hr*ng/mL for Group 2, 256.6-2530.1 hr*ng/mL for Group 3 and 559.4-4894.9 for Group 4.

A NOEL could not be determined; the no-observed-adverse-effect level (NOAEL) was considered to be 300 mg/kg/day (6000 mg/m2/d) for both sexes. A STD could not be calculated in this study and is likely to be higher than 300 mg/kg/day (6000 mg/m2/d).

The hydrochloride salt form of MP470 has been demonstrated to have potent inhibitory activity against many tyrosine kinases involved in tumor progression and survival, and good tumor inhibitory activity in murine tumor models. The salt form is well absorbed after oral administration and has a good pharmacokinetic profile. It is well tolerated in both rat and dog following multiple doses with a wide margin of safety. The NOEL following repeated dosing for 28 days are 60 mg/kg/d (360 mg/m2/d) for male rats and 20 mg/kg/d (120 mg/m2/d) for female rats. In dogs the NOAEL was 300 mg/kg/day (6000 mg/m2/d) for both sexes. As the drug is relatively non-toxic a severely toxic dose could not be determined, it is likely to be higher than the highest doses in the 28-day toxicology studies (600 and 1200 mg/m2/d in female and male rat respectively, and 6000 mg/m2/d in dogs).

Effects of MP470.HCl on Rad51 Levels In Vivo

Dose-response effects of MP470.HCl on Rad51 were evaluated in normal beagle dogs that were administered MP470.HCl orally. Colon and skin tissues were obtained from five different groups, including vehicle control group, three groups of differing dose levels of MP470.HCl following a 28 day daily treatment with MP470.HCl, and a post-treatment recovery group two weeks after treatment daily for 28 days with 300 mg/kg of MP470.HCl. These tissue specimens were stained for Rad51 using immunohistochemistry (IHC) techniques on an automated staining platform. A mouse Anti-Rad51 antibody was used for this purpose. Positive and negative controls were used to validate the staining procedure. The data is reported as a percentage based on the scoring of the staining intensity by a board-certified pathologist. Staining intensity was reported as mean percent for n=3 in all cases except the recovery group, where n=1. The following results were obtained:

| Dose Level (mg/Kg) | Colon (%) | Skin (%) |
|---|---|---|
| Vehicle | 71 | 20 |
| 30 | 61 | 14 |
| 100 | 56 | 17 |
| 300 | 35 | 11 |
| Recovery (2 wk post treatment with 300 mg/kg) | 19 | 7 |

Thus, dose-dependent suppression of Rad51 was observed in tissues of dogs treated with MP470.HCl. A measurable response in skin would allow for the use of skin biopsies in patients being treated with MP470.HCl for clinical validation of the biomarker effect.

What is claimed is:

1. A pharmaceutical formulation for oral administration comprising a pharmaceutically acceptable excipient and a hydrochloride salt of MP470, wherein the MP470 has the following structure:

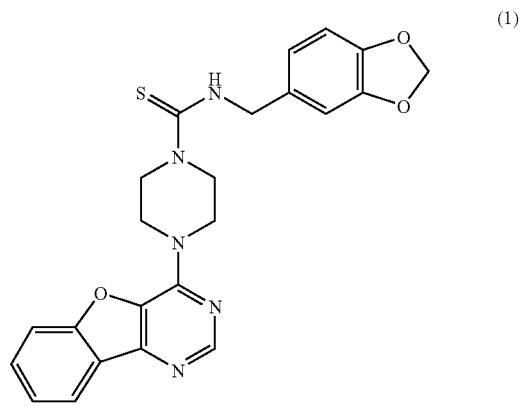

2. The pharmaceutical formulation of claim 1, wherein the HCl salt of MP470 comprises a crystalline form characterized by an X-ray diffraction pattern having diffraction peaks (2θ) at 8.1°, 13.0°, and 24.6°.

3. The pharmaceutical formulation of claim 2 wherein said salt is further characterized by a melting endotherm of 180-210° C. as measured by differential scanning calorimetry at a scan rate of 10° C. per minute.

4. The pharmaceutical formulation of claim 2 wherein said salt is further characterized by a melting endotherm of 185-200° C. as measured by differential scanning calorimetry at a scan rate of 10° C. per minute.

5. The pharmaceutical formulation of claim 1, wherein the HCl salt of MP470 comprises a crystalline form characterized by an X-ray diffraction pattern having diffraction peaks (2θ) at 9.5°, 10.4°, 11.4°, 14.1°, and 25.5°.

6. The pharmaceutical formulation of claim 1 wherein the pharmaceutical composition is in a solid form in which the salt is mixed with carriers or a liquid form in which the salt is dissolved.

7. The pharmaceutical formulation of claim 6 wherein the salt is dissolved in a non-aqueous solvent that comprises glycerin, propylene glycol, polyethylene glycol, or a combination thereof.

8. The pharmaceutical formulation of claim 6 wherein the pharmaceutical formulation is an aqueous solution in which the salt is dissolved.

9. The pharmaceutical composition of claim 6, wherein the pharmaceutical composition is in an oral dosage form.

10. The pharmaceutical formulation of claim 9, wherein the oral dosage form is tablet, capsule, suspension or liquid.

11. A pharmaceutical formulation for oral administration comprising a pharmaceutically acceptable excipient and a hydrochloride salt form of MP470, wherein the MP470 has the following structure:

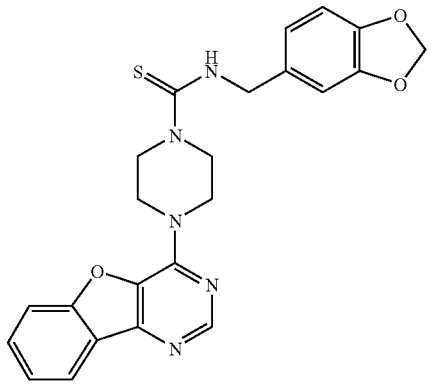

(1)

and wherein the salt form of MP470 in the formulation has a decreased toxicity and an increased oral bioavailability relative to the free base form of MP470.

12. The pharmaceutical formulation of claim 11, wherein the increased oral bioavailability is at least 50% higher than in the free base form of MP470.

13. The pharmaceutical formulation of claim 11, wherein the increased oral bioavailability is at least 75% higher than in the free base form of MP470.

* * * * *